United States Patent
Koyakutty et al.

(10) Patent No.: US 9,545,382 B2
(45) Date of Patent: Jan. 17, 2017

(54) NANOPARTICLE FORMULATIONS FOR DELIVERING MULTIPLE THERAPEUTIC AGENTS

(71) Applicant: Amrita Vishwa Vidyapeetham University, Kochi (IN)

(72) Inventors: Manzoor Koyakutty, Kochi (IN); Giridharan Loghanathan Malarvizhi, Kochi (IN); Shantikumar Nair, Kochi (IN)

(73) Assignee: Amrita Vishwa Vidyapeetham University, Center for Nanosciences and Molecular Medicine, Ponekkara (PO), Kochi (IN)

( * ) Notice: Subject to any disclaimer, the term of this patent is extended or adjusted under 35 U.S.C. 154(b) by 0 days.

(21) Appl. No.: 14/732,716

(22) Filed: Jun. 6, 2015

(65) Prior Publication Data

US 2015/0342896 A1 Dec. 3, 2015

Related U.S. Application Data

(63) Continuation-in-part of application No. 14/465,521, filed on Aug. 21, 2014, now Pat. No. 9,402,918, which is a continuation of application No. PCT/IN2013/000108, filed on Feb. 19, 2013, application No. 14/732,716, which is a continuation-in-part of application No. PCT/IN2013/000141, filed on Mar. 12, 2013.

(51) Int. Cl.
*A61K 9/51* (2006.01)
*A61K 47/48* (2006.01)
*A61K 45/06* (2006.01)
*A61K 31/44* (2006.01)
*A61K 31/704* (2006.01)

(52) U.S. Cl.
CPC ............... *A61K 9/51* (2013.01); *A61K 31/44* (2013.01); *A61K 31/704* (2013.01); *A61K 45/06* (2013.01); *A61K 47/483* (2013.01); *A61K 47/48284* (2013.01); *A61K 47/48315* (2013.01); *A61K 47/48884* (2013.01)

(58) Field of Classification Search
None
See application file for complete search history.

(56) References Cited

U.S. PATENT DOCUMENTS

2007/0053845 A1* 3/2007 Sengupta ............. A61K 9/1271 424/46
2010/0112077 A1* 5/2010 Desai .................. A61K 9/0019 424/499

OTHER PUBLICATIONS

Llovet et al., "Randomized phase III trial of sorafenib versus placebo in patients with advanced hepatocellular carcinoma (HCC)", J. Clin. Oncol., 2007 ASCO Annual Meeting Proceedings (Abstract), vol. 25, No. 18S (2007).*

* cited by examiner

*Primary Examiner* — Bethany Barham
*Assistant Examiner* — Barbara Frazier
(74) *Attorney, Agent, or Firm* — Convergence Intellectual Property Law P.C.; Jonathan Garfinkel

(57) ABSTRACT

A formulation for treating a patient with hepatocellular carcinoma is disclosed. The formulation comprises therapeutic agents in the form of nanoparticles containing one or more proteins or polysaccharides. The therapeutic agent is conjugated to an active targeting agent causing the formulation to preferentially segregate to the hepatocellular carcinoma tissue to release the therapeutic agents. Methods of treating hepatocellular carcinoma using the formulations are also disclosed.

3 Claims, 18 Drawing Sheets

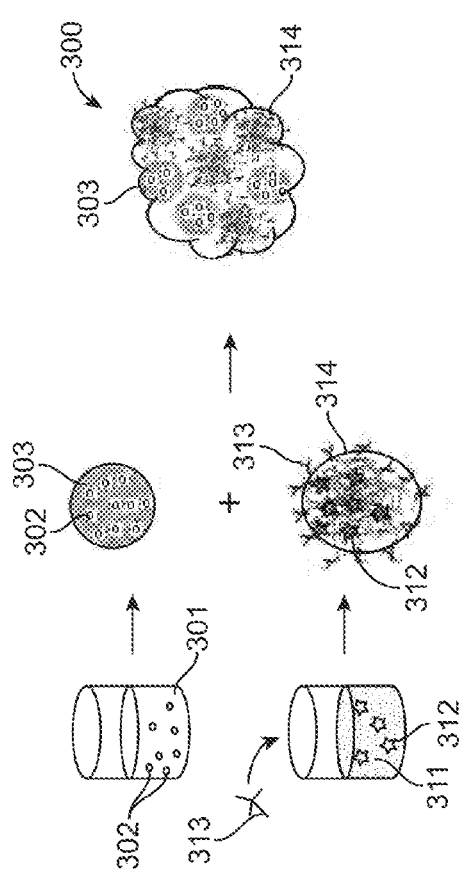
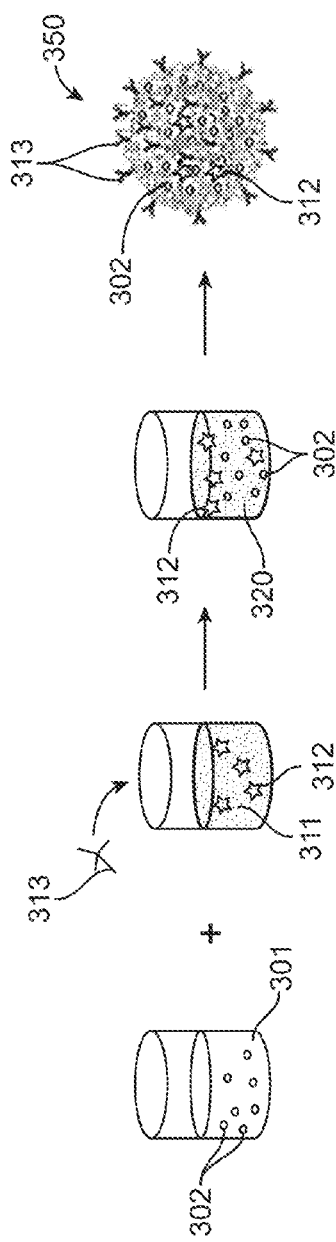
FIG. 3A
FIG. 3B

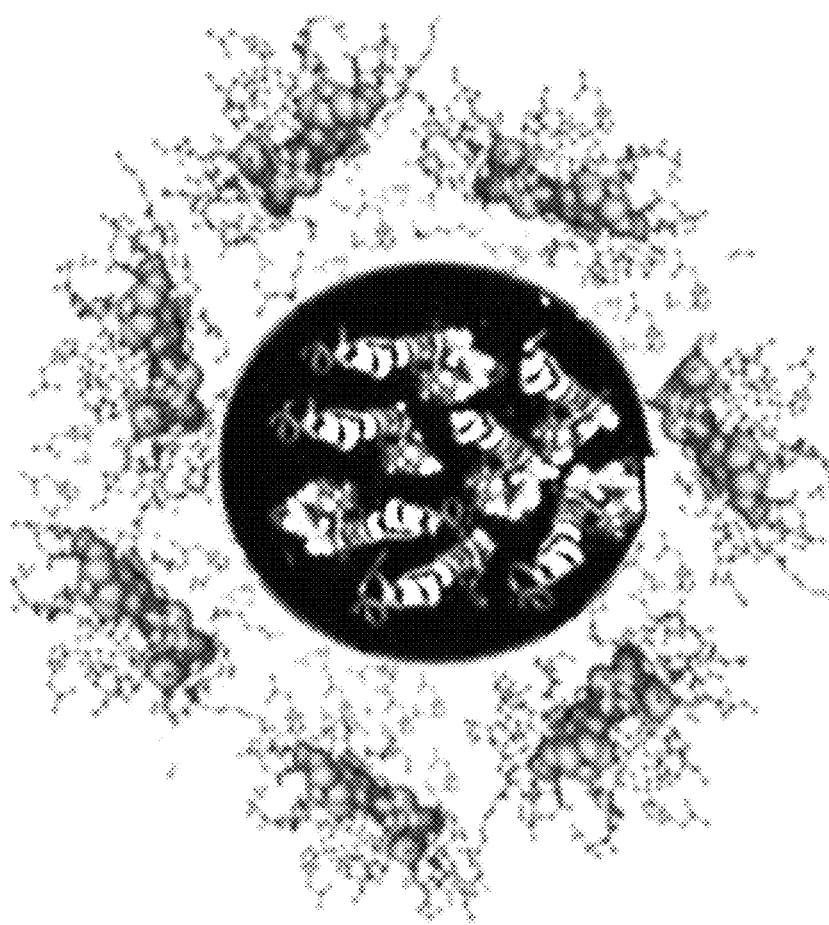
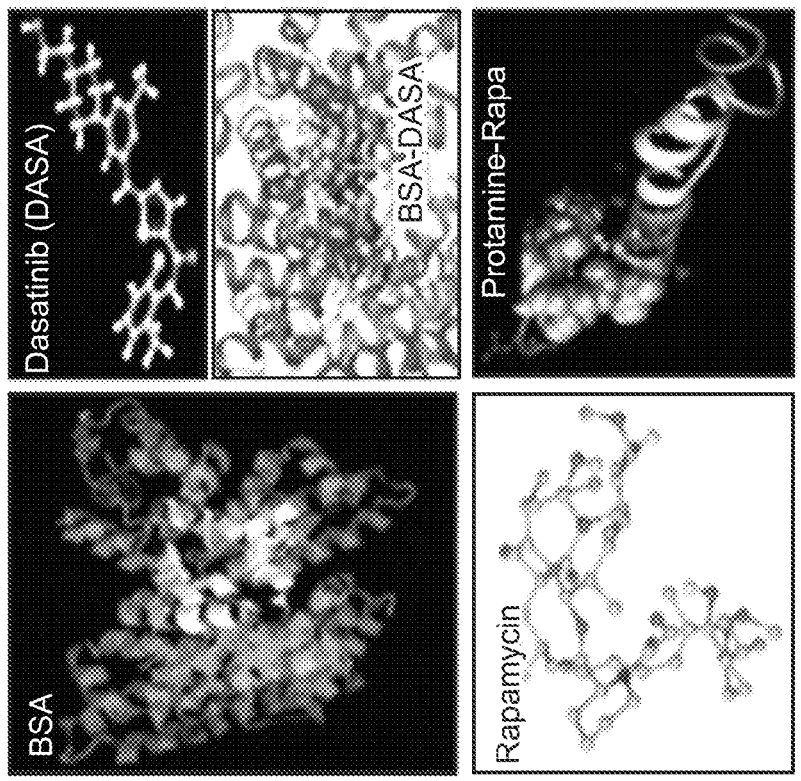
FIG. 5B
FIG. 5A (i) Au nanocluster doped albumin
(ii) Au-BSA-DASA
(iii) (Prt-RAPA)-(Au-BSA-DASA)

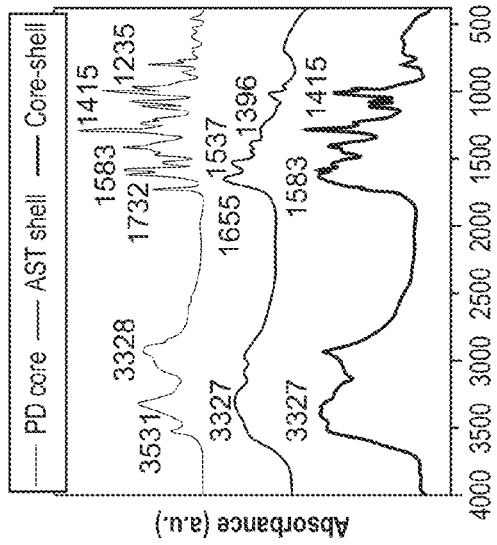
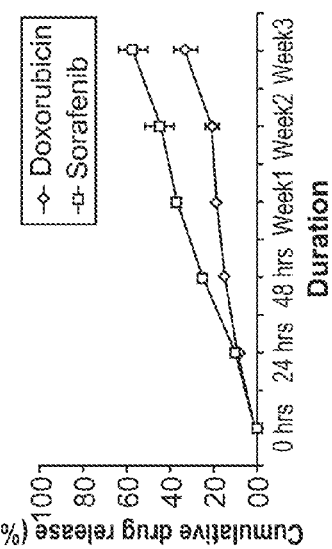
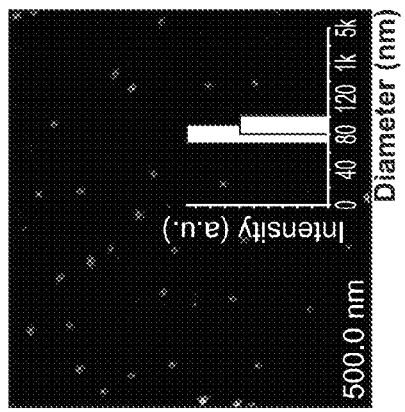
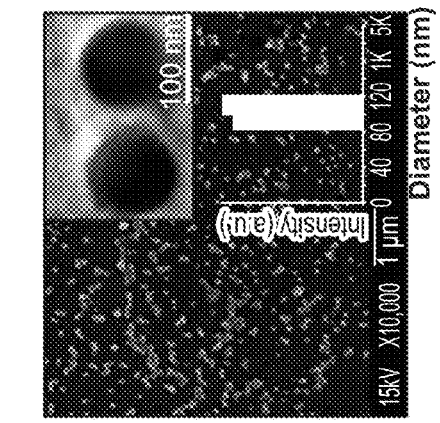
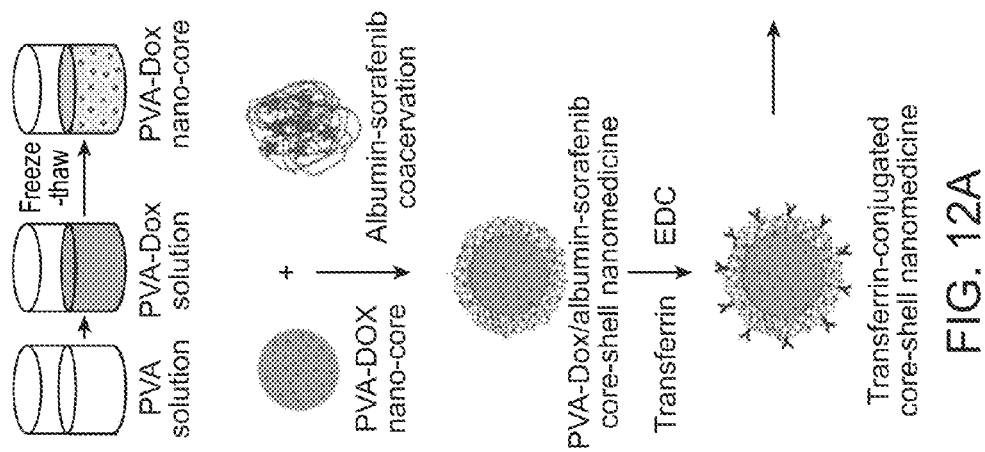

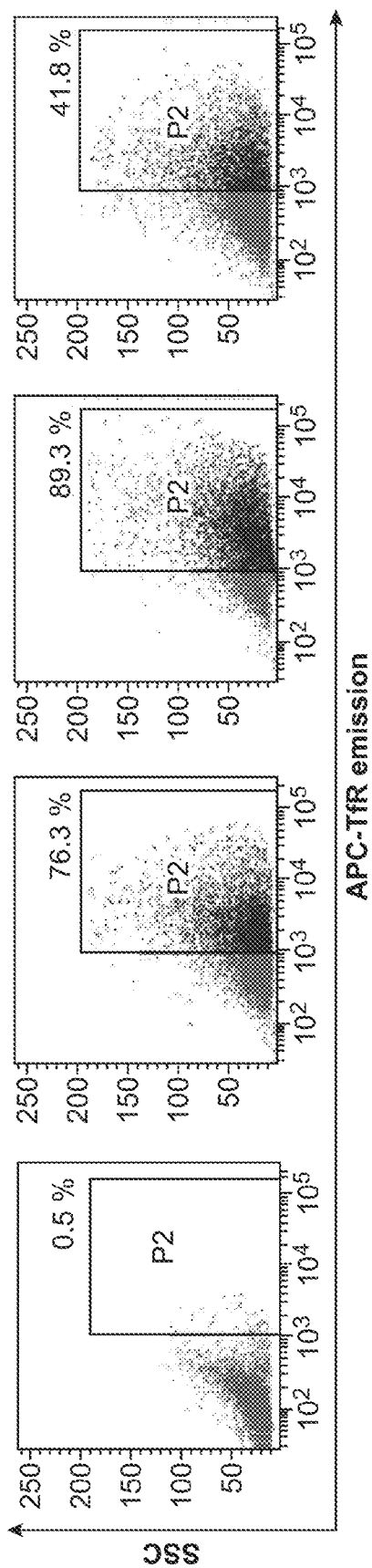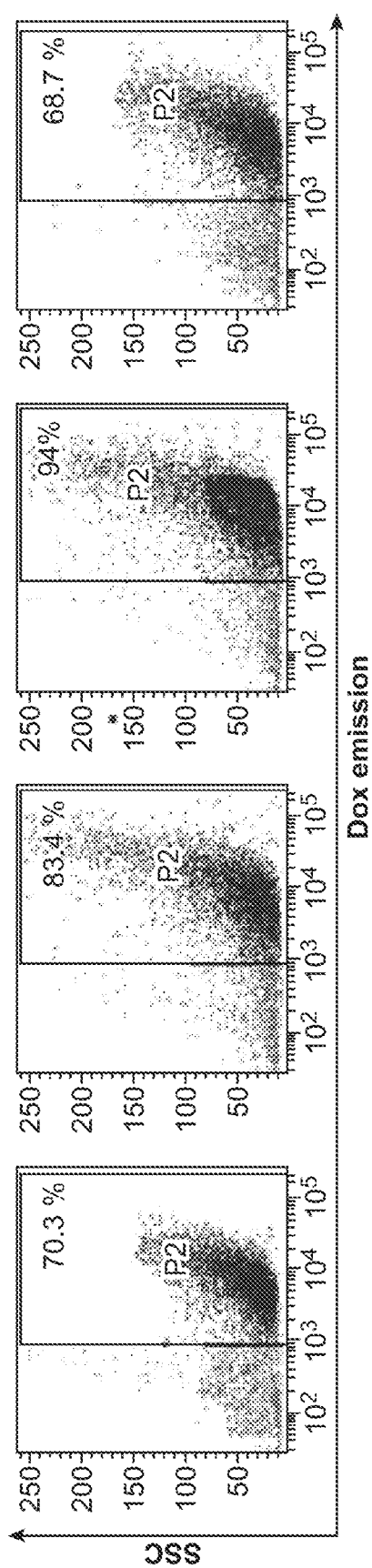

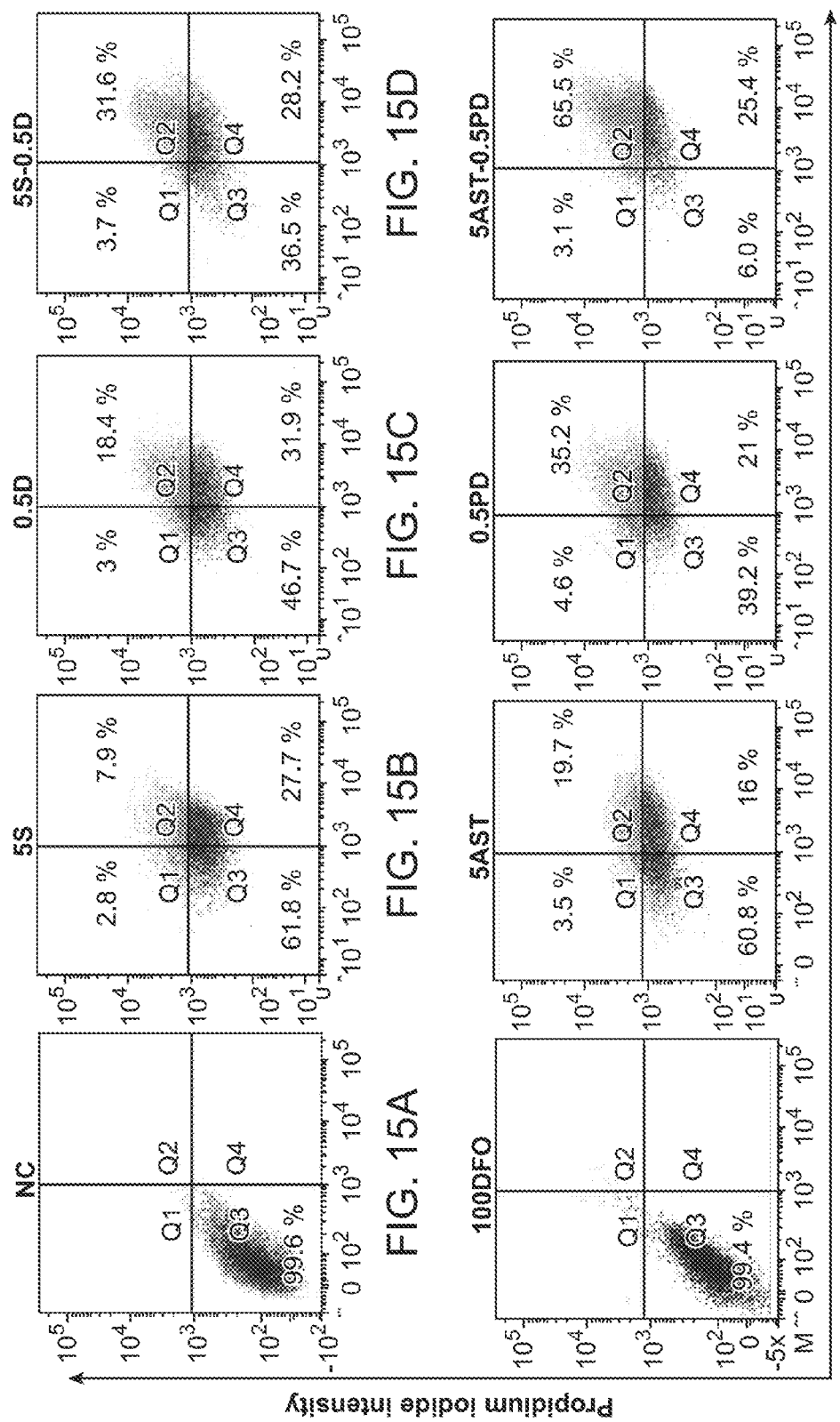

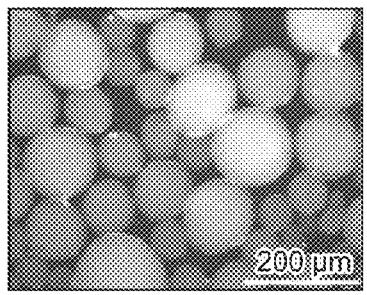 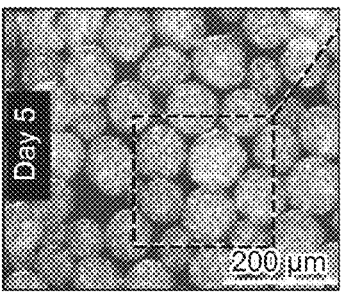 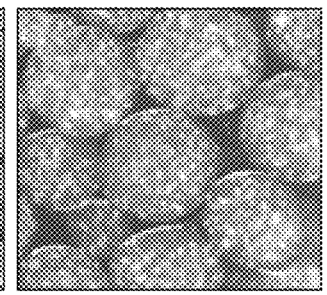
FIG. 16A  FIG. 16B  FIG. 16C
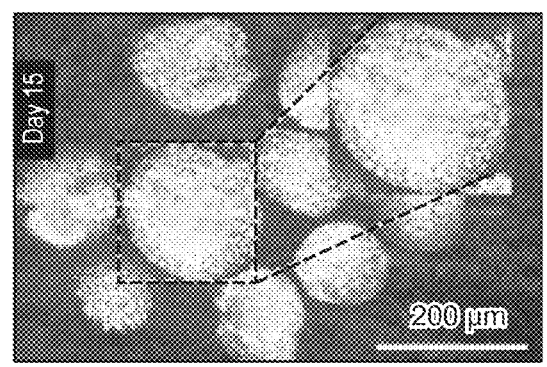 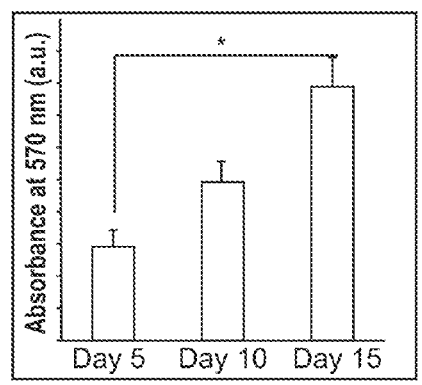
FIG. 17A  FIG. 17B
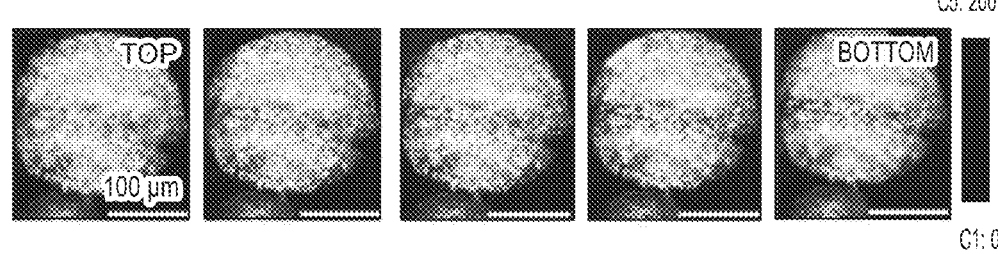
FIG. 18A  FIG. 18B  FIG. 18C  FIG. 18D  FIG. 18E

NANOPARTICLE FORMULATIONS FOR DELIVERING MULTIPLE THERAPEUTIC AGENTS

CROSS-REFERENCES TO RELATED APPLICATIONS

This application is a continuation-in-part of PCT international application No. PCT/IN2013/000141 filed on Mar. 12, 2013, which claims priority to Indian patent application No. 2550/CHE/2012, filed on Jun. 27, 2012, and a continuation-in-part of U.S. application Ser. No. 14/465,521 filed on Aug. 21, 2014, which is a continuation of PCT international application No. PCT/IN2013/000108 filed on 19 Feb. 2013, which claims priority to Indian patent application No. 644/CHE/2012, filed on 21 Feb. 2012, the full disclosures of which are incorporated herein by reference.

FIELD OF THE INVENTION

This invention relates generally to core-shell particle formulations for delivering multiple therapeutic agents, and more particularly, core-shell particle formulation configured to independently release therapeutic agents from the core and the shell. The core-shell particle bearing therapeutic agents are envisaged to enable treatment against diseases such as cancer, inflammatory and auto-immune diseases.

DESCRIPTION OF THE RELATED ART

Successful management of diseases requires development of drug delivery systems with maximum therapeutic benefits. Most of the diseases including cancer are associated with deregulation of multiple signaling pathways. An essential requirement of drug delivery systems is the controlled delivery of a therapeutic molecule to the diseased site at therapeutically relevant concentrations. The site-specific delivery of multiple therapeutic molecules to the diseased site using a single carrier vehicle in a specified steady concentration for prescribed time duration improves the efficacy of the therapeutic molecule and thus reduces the possible side effects, thus improving the therapeutic index. The release kinetics of the therapeutic molecule is often dependent upon the encapsulating material/carrier properties, drug-particle interactions or through some other trigger mechanisms, which assist in the drug release. Design of drug delivery systems generally involves encapsulation of the drug within a suitable shell to form particles of suitable size. The drug can be distributed either within a hollow shell or within the solid particle.

The advantages of such encapsulation is the control over release kinetics, giving the ability for slow release over a long period of time, and protection of the drug from a potentially degrading biological environment. Recent advancements in nanotechnology have revolutionized the field of drug delivery. The advantages of nanoparticles over conventional systems of drug delivery include, high surface area to volume ratio enabling better cellular uptake, thereby affecting intracellular pathways of action compared to that of free molecules and the ability to efficiently bio-functionalize the particulate surface with cell-specific targeting ligands for specific attachment to particular cells which require drug action. Protein based drug delivery systems are ideal platforms for the delivery of multiple therapeutics for in vivo applications due to their amphiphilic nature, biocompatibility and biodegradability coupled with low toxicity. The degradation products of the carrier system will be amino acids, which are well tolerated by the human body.

Depending upon the nature of the molecules to be encapsulated, a wide choice of preparations is available such as desolvation, heat denaturation, coacervation, cross-linking, nano precipitation emulsification, etc. The particle size of the system can be fine-tuned with slight changes in synthesis parameters such as temperature, pH, etc. Moreover, the nanoparticles possess greater stability during storage or in vivo after administration, and provide surface functional groups for conjugation to cancer targeting ligands. They also are suitable for administration through different routes.

US201001122077 describes combination therapy methods of treating proliferative diseases like cancer with a first therapy comprising of effective amount of a taxane in a nanoparticle composition, with second therapy such as radiation, surgery, administration of chemotherapeutic agents such as anti-VEGF antibody or combinations thereof.

Most of the FDA approved nanoformulations and other drug delivery systems reported till date are single agent delivery vehicles which pose structural constraints in encapsulation and release of multiple payloads in optimal concentrations at the tumor site. Encapsulation of more than one drug in the same nano-carrier may elicit undesirable drug-drug interaction which might alter the pharmacology of both the drugs, resulting in inefficacy of the drugs. The conventional chemotherapy regimen in an attempt to reduce the tumor volume, do not discriminate between rapidly dividing normal cells and tumor cells, thus leading to severe side-effects.

Therefore, there remains a need for a drug delivery system for delivering combination therapies so that each agent provides the desired maximal effect. Moreover, the drug delivery system must deliver multiple therapeutic agents and independently release these therapeutic agents to the targeted diseased sites.

SUMMARY OF THE INVENTION

Nanoparticle particle formulations for delivering multiple therapeutic agents are disclosed. In one embodiment, a formulation for treating a patient with hepatocellular carcinoma is disclosed, comprising doxorubicin as a first therapeutic agent and sorafenib as a second therapeutic agent. The first and second therapeutic agents are in the form of nanoparticles comprising one or more proteins or polysaccharides. The formulation is conjugated to an active targeting agent.

In one embodiment, the formulation comprising doxorubicin and the sorafenib as therapeutic agents are loaded onto the same nanoparticle or onto separate nanoparticles that are aggregated. In one embodiment, the doxorubicin is loaded onto core nanoparticles comprising the one or more proteins or polysaccharides and the sorafenib is loaded onto a shell comprising the one or more proteins, covering the core nanoparticles. In some embodiment, the formulation comprising the particle is configured to independently release the therapeutic agents from the core and the shell. In some embodiments the active targeting agent is transferrin.

The polysaccharides in the formulation are selected from the group consisting of polyethylene glycol, polyethylene oxide, starch, hyaluronic acid, gelatin, poly(vinyl alcohol-co-ethylene), poly(vinyl butyral-co-vinyl alcohol-co-vinyl acetate), poly(vinyl chloride-co-vinyl acetate-co-vinyl alcohol), poly-N-para-vinylbenzyl-lactonamide, chondrotin sulphate, dextran, cyclodextrin, polyglycolide, glycolide L-lactide copolymers, glycolide/trimethylene carbonate copolymers, poly-lactides, poly-L-lactide, poly-DL-lactide, L-lactide/DL-lactide copolymers, lactide/tetramethyl-glycolide copolymers, poly-caprolactone, poly-valerolacton, poly-hydroxy butyrate, polyvinyl alcohol, polyhydroxy valerate, poly-N-isopropylacrylamide and lactide/trimethylene carbonate copolymers, polyvinyl pyrrolidone, polyethylene imine, chitosan, carboxymethyl chitosan, chitin, pullulan, dextrose, cellulose, carboxymethyl cellulose, alginate, glucomannan, poly-γ-glutamic acid, poly-propylene glycol, poly-acrylic acid, poly(lactic-co-glycolic acid), poly-caprolactone, poly-valerolactone, poly-hydroxy butyrate, polyvinylpyrrolidone, polyethyleneimine, and lactide/trimethylene carbonate copolymers.

The proteins in the formulation are selected from the group consisting of human serum albumin, bovine serum albumin, protamine, transferrin, lactoferrin, fibrinogen, gelatin, mucin, soy protein, apoferritin, ferritin, lectin, gluten, whey protein, prolamines, gliadin, hordein, secalin, zein, and avenin.

In some embodiments the size of the particle is 1-1000 nm. In some embodiments the formulation results in cytotoxicity greater than 90% at minimum concentrations of 2 µM doxorubicin in core and 5 µM sorafenib in shell against hepatocellular carcinoma cells.

In one embodiment a method of treating a patient for hepatocellular carcinoma with a formulation comprising therapeutic agents is disclosed. The method comprises the steps of a. forming a first solution of doxorubicin comprising one or more proteins or polysaccharides and b. conjugating sorafenib with an active targeting ligand with one or more proteins to form a second solution. In the next step c. a formulation comprising nanoparticles using the first and the second solutions is produced. In step d. the nanoparticle formulation is administered to a patient such that the targeting ligand causes the formulation to preferentially segregate to the hepatocellular carcinoma tissue to release the therapeutic agents.

In one embodiment of the method the producing the nanoparticle formulation comprises one of precipitating nanoparticles comprising the doxorubicin and the sorafenib separately from the first and the second solutions and aggregating the nanoparticles into the nanoparticle formulation. In one embodiment the nanoparticle is produced by mixing the first and the second solutions and precipitating composite nanoparticles to produce the nanoparticle formulation. In another embodiment producing the nanoparticle formulation includes forming a core nanoparticle comprising doxorubicin using the first solution and a shell comprising sorafenib over the core nanoparticle using the second solution to form the nanoparticle formulation.

In one embodiment the ligand for targeting comprises transferrin. In various embodiments the formulation is administered by local injection, intratumoral, intraarterial intravenous, intrathecal, intracavitary subcutaneous, intramuscular or oral delivery. In some embodiments the formulation is delivered as an embolizing agent to the hepatocellular carcinoma tissue. The method of in its various embodiments results in cytotoxicity greater than 90% against hepatocellular carcinoma tissue at minimum concentrations of doxorubicin in core of 2 µM and sorafenib in shell of 5 µM.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 3A, 3B and 3C illustrate nanoparticle formulations for treating a patient with hepatocellular carcinoma according to some embodiments.

FIGS. 5A and 5B show an example with two rapamycin and dasatinib docked protamine and albumin respectively, in a core-shell architecture, FIG. 5A shows computational modeling of albumin-dasatinib and protamine-rapamycin interactions, FIG. 5B shows computationally designed structure of (protamine-rapamycin) (albumin-dasatinib) core-shell nanoparticles.

FIGS. 10A-C show the destabilization of cytoskeleton and distortion of cellular morphology by (protamine-rapamycin) and (albumin-dasatinib) core-shell system as depicted by actin staining.

FIG. 12A is a schematic on the processing steps of core-shell nanomedicine and FIG. 12B shows atomic force microscopy (AFM) image of PVA-Dox.

FIG. 12B represents a DLS graph showing hydrodynamic diameter of the nano-core (~90 nm).

FIG. 12C shows scanning electron microscopy (SEM) image for the morphology of the core-shell nanomedicine. Inset of FIG. 12C represents DLS graph showing hydrodynamic diameter (~110 nm), and TEM image showing unique protein nano-shell (~20 nm) formed over the polymer core.

FIG. 12D shows Fourier transform infrared (FT-IR) spectra of PVA-Dox nano-core (PD), TfR-targeted albumin-sorafenib nano-shell (AST), and core-shell nanomedicine and FIG. 12E shows controlled release of doxorubicin and sorafenib from the core-shell nanomedicine in cell-free aqueous medium.

FIG. 13A-FIG. 13D show transferrin receptor expression studies in HepG2 cells.

FIG. 13E-FIG. 13H show intercellular uptake studies of core-shell nanomedicine in HepG2 cells.

FIG. 15A-FIG. 15H show the apoptotic cells quantified by flow cytometry analysis before and after treatment with different concentration of therapeutic agents.

FIG. 16A shows the morphology of cell-free alginate-collagen spheroids, (FIG. 16B) HCC cells embedded 3D spheroids (Day 5) and FIG. 16C shows magnified image of uniform cell distribution throughout the spheroids.

FIG. 17A shows 3D spheroids revealing tumor tissue-like architecture (Day 15), Inset of FIG. 17A represents magnified image of HCC tissue in spheroid. (FIG. 17B) Alamar blue cell viability assay shows time-dependent increase in resorufin fluorescence by the proliferating cells in the spheroids.

FIG. 18A-FIG. 18E illustrate the depth-by-depth confocal view from anterior (top) to posterior side (bottom) of a representative liver tumor spheroid.

DETAILED DESCRIPTION OF THE EMBODIMENTS

Figure 1:
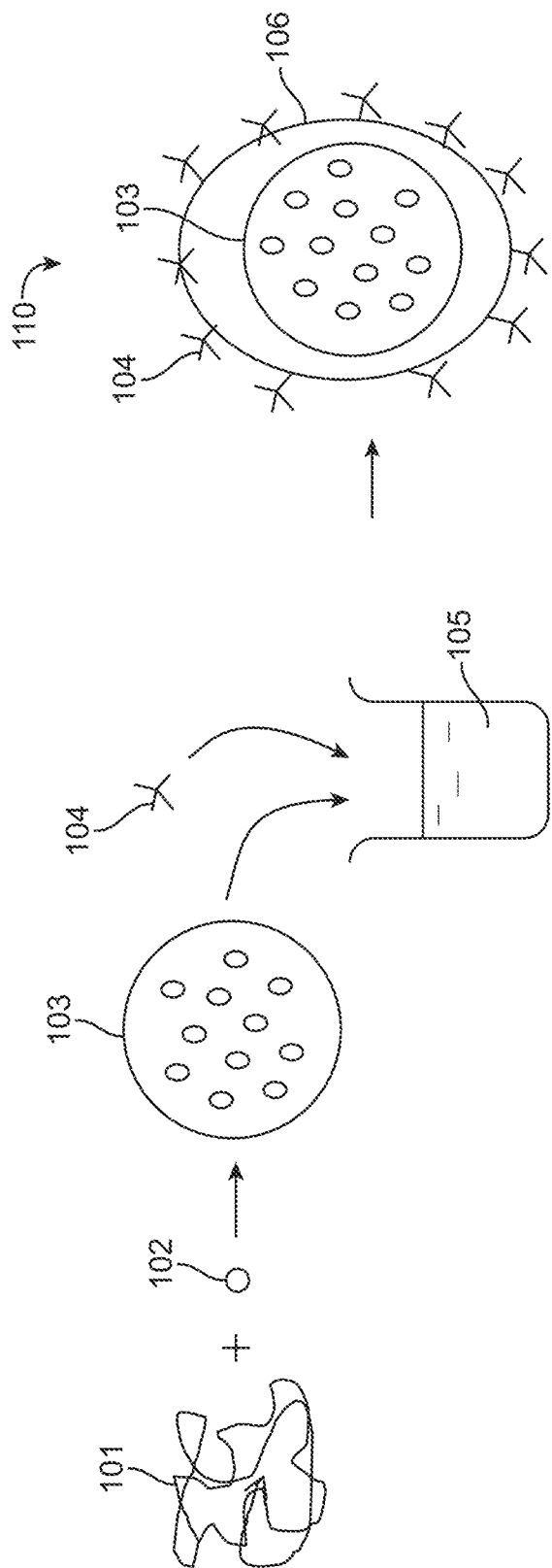
FIG. 1 illustrates a nanoparticle core-shell formulation according to one embodiment.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The term "nanomedicine" as used herein may refer to nanoparticles of two or more proteins, measuring size about 1-1000 nm capable of delivering multiple anti-cancer agents such as chemotherapeutic drugs, small molecule inhibitors etc., in different combinations of at least one small molecule kinase inhibitor and one chemotherapeutic drug or suitable combination of two small molecule inhibitors/chemotherapeutic drugs together. In one embodiment the nanoparticles have a size around 1-500 nm. In another embodiment the nanoparticles have a size around 1-200 nm in size.

"Protein-protein core-shell nanomedicine" may refer to nanomedicine constructs comprising a nano-core formed by one type of protein loaded with one type of chemotherapeutic drug and an outer nano-shell formed by another type of protein loaded with another drug.

Therapeutics may be refer to synthetic drugs including cytotoxic drugs and small molecule kinase inhibitors, phytochemicals or nucleic acid drugs such as siRNAs, shRNAs, miRNAs, PNAs, DNA, DNAzymes, ribozymes, or prodrugs thereof, that have a therapeutic effect against diseases including cancer, inflammatory and auto-immune diseases and the like.

The proposed invention relating to core-shell particle formulation for delivering multiple therapeutic agents is described in the following sections referring to the sequentially numbered figures. The above-mentioned objectives are achieved through the core-shell particle bearing therapeutic agents specifically targeted to the preferred site of action and configured to controllably release therapeutic agents.

Figure 2:
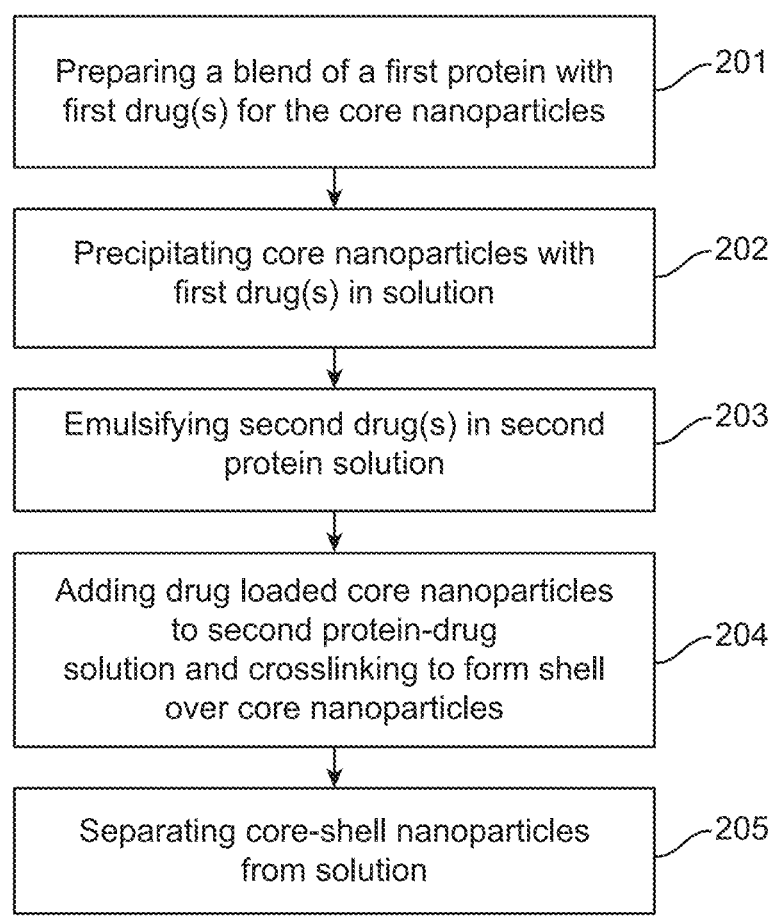
FIG. 2 is a schematic of the method of preparing a core-shell formulation of the invention according to one embodiment.

In one embodiment, core-shell particles for delivering multiple therapeutic agents and methods for their preparation are disclosed, as shown in FIGS. 1 and 2, respectively. As shown in FIG. 1, in one embodiment, the particles of the invention comprise one or more proteins to form a core 101 and one or more proteins forming a shell 106. In various embodiments, the core 101 and the shell 106 each comprise one or more therapeutic agents. In one embodiment of the invention illustrated in FIG. 2, the particle is obtained using the steps shown in the figure. In step 201, a protein precursor solution of the core 101 is reacted with the first therapeutic agent 102 and precipitated to form the drug-loaded core nanoparticles 103 in step 202. In step 203, a second therapeutic agent 104 is blended with a second protein solution 105 for forming the protein shell. The drug-loaded core nanoparticles 103 are added to the blended second protein solution 105 in step 204, in which the therapeutic agent 104 is incorporated into the protein 105 and crosslinked to form a shell 106 around the core 103. Finally, in step 205, the fully formed core-shell nanoparticles 110 with the first therapeutic agent 102 loaded in the core and the second therapeutic agent 104 loaded in the shell are separated from solution for therapeutic use.

In various embodiments, the protein 105 forming the core 101 and shell 106 is chosen from human serum albumin, bovine serum albumin, protamine, transferrin, lactoferrin, fibrinogen, gelatin, mucin, soy protein, apoferritin, ferritin, lectin, gluten, whey protein, prolamines such as gliadin, hordein, secalin, zein, avenin, ovalbumin, histone, fibrin, collagen, and their derivatives or combinations thereof.

In various embodiments the protein nanoparticle or the protein shell is formed by a method that is one of nano-precipitation, coacervation, self-assembly, cross-linking, spray drying, electrospray, emulsion desolvation, snap injection, etc. In some embodiments, one or both of the proteins in the core-shell nanoparticle 110 are doped/loaded/embedded with metallic nanoclusters comprising one or more of gold, silver, platinum, copper, iron, manganese, gadolinium, europium or terbium for the purpose of tracking the nanoparticles in vivo using one or more of optical, magnetic or x-ray contrast. In some embodiments, the prepared core-shell nanoparticle 110 is purified by centrifugation and lyophilisation.

In one embodiment, the total size of the core-shell particle is of 1-1000 nm. In various embodiments, the core and shell are loaded with one or more small molecule kinase inhibitors or chemotherapeutic drugs. In various embodiments, the shell comprises either hydrophilic or hydrophobic therapeutic agents, or both types of agents.

In one embodiment, the core and shell are loaded with different therapeutic agents comprising synthetic chemotherapeutic drugs including cytotoxic drugs or one or more small molecule kinase inhibitors or phytochemicals or nucleic acid drugs such as deoxyribozymes, ribozymes, siRNA, shRNA, DNA, PNAs, or miRNAs or combinations thereof.

In various embodiments, the chemotherapeutic drug is chosen from one or more of demethylation agents, retinoids, antimetabolites, antimicrotubule agents, anti-angiogenesis agents, alkylating agents, biological response modifiers, antitumor antibiotics, proteasome inhibitors, topoisomerase I inhibitors, topoisomerase II inhibitors, and phytochemicals including curcumin, theobromine, theophylline, anthocyanins (cyanidin, malvidin), carotenoids (Alpha-carotene, Beta-carotene, Beta-cryptoxanthine, luetin, Xeaxanthin, astaxanthin, lycopene), hydroxylcinnamic acids (Chicoric acid, coumarin, ferulic acid, scopoletin), flavones (apigenin, chrysin, luteolin, Daidzein, Genistein), flavonols (galalgin, fisetin), flavanones (eriodictyol, hespertin, naringenin), anthocyanidines (cyanidin, pelargonidin, delphinidin, peonidin, malvidin), isoflavonoids (genistein, daidzein, glycitein, formononetin), flavanoles (catechin, epicatechin, epigallocatechin, epicatechin gallate, epigallocatechin gallate), lignans (Silymarin), phenolic acids (capsaicin, ellagic acid, gallic acid, rosmarinic acid, tannic acid) organosulfides (allicin, glutathione, indole-3-carbinol, isothiocyanate sulforaphane), phytosterols (Beta-Sitosterol), stylbenes (Pterostilbene, Resveratrol), xanthophylls (Astaxanthin, Beta-Cryptoxanthin), tannins, saponins, steroids, phlobatannin, terpenoids (Geranlol, limenene), flavonoids (epicatechin, Hesperidin, Isohamnetin, Kaempferol, Myricetin, galangin, fisetin) Naringin, Nobiletin, Proanthocyanidins, Quercetin, Rutin, Tangeretin), hydroxyl benzoic acids (gallic acid, protocatechuic acid, vannilic acid, syringic acid), hydroxyl cinnamic acids (p-coumaric acid, caffeic acids, ferulic acid, sinapic acid), glycosides, hormones, immunomodulators, monoclonal antibodies, aromatase inhibitors, glucocorticosteroids, cytokines, enzymes, anti-androgen molecules, epigenetic modifiers, imatinib, sorafenib, Regorafenib, Raf265, Vemurafenib, Dabrafenib, Encorafenib, nilotinib, erlotinib, gefitinib, dasatinib, everolimus, cyclophosphamide, methotrexate, 5-fluorouracil, doxorubicin, cisplatin, hydroxyurea, leucovorin calcium, tamoxifen, flutamide, asparaginase, altretamine, mitotane, procarbazine hydrochloride, mechlorethamine, thioguanine, carmustine, lomustine, temozolomide, melphalan, chlorambucil, streptozocin, methotrexate, vincristine, bleomycin, vinblastine, vindesine, dactinomycin, daunorubicin, Lenalidomide, L-asparginase, tamoxifen or anti-proliferative agents such as rapamycin, paclitaxel or anti-angiogenesis agents such as avastin, or inhibitors of tyrosine kinase including epidermal growth factor receptor (EGFR), vascular endothelial growth factor receptor (VEGFR), platelet derived growth factor receptor (PDGFR), fibroblast growth factor receptor (FGFR), Rous sarcoma oncogene/Breakpoint cluster region/Abl (Src-bcr-abl), Insulin-like growth factor 1 receptor (IGF-1R), FLT-3, HER-2, STATS, c-Kit, c-Met, ALK, RAS, RAF, mutant B-RAF inhibitor, ETA receptor inhibitor, HIF inhibitor, Syk inhibitor, Tie2 kinase inhibitor and the like), Vascular disrupting agents (e.g. plinabulin), cell cycle/check point inhibitors like polo-like kinase (PLK) inhibitor (e.g. volasertib), cyclin dependent kinase (CDK) inhibitors (e.g. seliciclib, indirubin etc.), topoisomerase inhibitors (e.g. adriamycin, camptothecin, etoposide, idarubicin, irinotecan, topotecan, doxorubicin, mitoxantrone etc.), microtubule inhibitors (e.g. docetaxel, paclitaxel, vincristine etc.), anti-metabolites (e.g. decitabine, gemcitabine, fludarabine etc.) telomerase inhibitors, DNA & RNA replication inhibitors (e.g. clarithromycin, cytarabine, mitoxantrone HCl, doxorubicin etc.,) dihydrofolate reductase inhibitor, HDAC inhibitor, Bcl-2 and TNF-α inhibitors, PARP inhibitors, MAPK inhibitors, PI3K/Akt/mTOR inhibitors, integrase and protease inhibitors, Wnt/Hedgehog/Notch inhibitors, cAMP, lipide signaling inhibitors (e.g. PKC, PIM etc.), TGF-β inhibitors, chemotherapeutic pro-drugs, antioxidant inhibitors like diethyl-dithiocarbamate, methoxyestradiol, 1-buthionine sulfoximine, 3-amino-1,2,4-triazole, lapatinib, sunitinib, meso-tetra(3-hydroxyphenyl)chlorine (m-THPC), hypericin, hormones, immunomodulators, monoclonal antibodies, aromatase inhibitors, glucocorticosteroids, cytokines, enzymes, anti-androgen molecules, epigenetic modifiers, nilotinib, erlotinib, gefitinib, dasatinib, everolimus, and combinations thereof.

In various embodiments, the nanoparticles comprising the therapeutic agents 102 and 104 are configured to be delivered as formulations with excipients suitable for local injection, or intravenous, subcutaneous, intramuscular or oral delivery. In some embodiments the formulations are configured to deliver therapeutic agents to targeted tissue by either passive or active targeting. In one embodiment, the active targeting is done by conjugating the core-shell formulation with targeting ligands such as monoclonal antibody against receptors such as, CD20, CD33, CD34, CD38, CD44, CD47, CD52 CD90, CD 123, CD 133, EGFR, PDGFR, VEGF, HER2, mTOR, PI3K-Akt, BCR-ABL, SRC, STATS, MAPK, HER2, transferrin receptors and like, peptides such as R.GD, CRGD, LyP-1, bombesin (BBN), FSH33, truncated human basic fibroblast growth factor (tbFGF), octreotide, folic acid, mannose, hyaluronic acid (HA), proteins such as transferrin, somatostatin, aptamers, glucose, sucrose, galactose, lactose, lactobionic acid, glycyrrhetinic acid, glycyrrhizic acid, sterylglucoside, peptides and their lactosylated or galactosylated derivatives or their combinations thereof. In one embodiment, the therapeutic agents are configured to be delivered to tissue from the shell and core either sequentially or simultaneously.

Figure 3C:
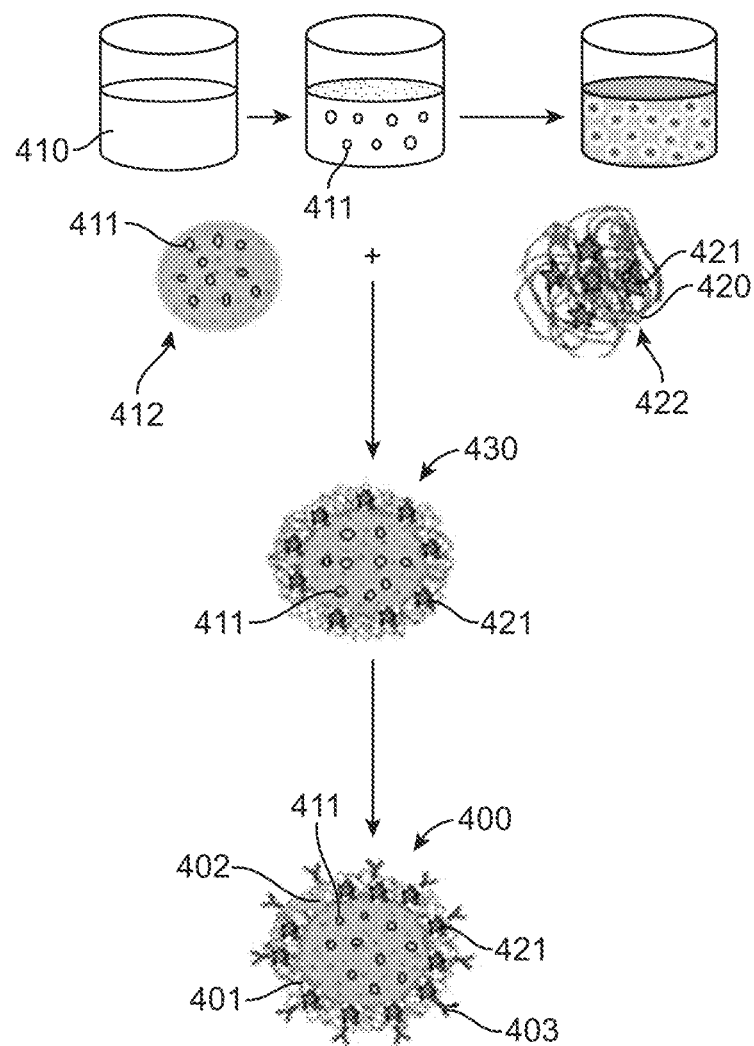

In embodiments illustrated in FIGS. 3A-3C, formulations for treating a patient with hepatocellular carcinoma are disclosed, comprising doxorubicin 302 and sorafenib 312 as therapeutic agents. The therapeutic agents are in the form of nanoparticles comprising one or more proteins or polysaccharides. The agents are conjugated to an active targeting agent, causing the formulations to preferentially segregate to the hepatocellular carcinoma tissue to release the therapeutic agents.

In one embodiment illustrated in FIG. 3A, the particle formulation 300 is obtained by aggregating nanoparticles 303 comprising doxorubicin 302 and nanoparticles 314 comprising sorafenib 312. Nanoparticles 303 are formed using a first solution 301 containing a polysaccharide in which the doxorubicin 302 is dissolved. In one embodiment the polysaccharide is polyvinyl alcohol (PVA). The second solution 311 is formed by adding solvent to albumin to form a solution in which sorafenib 312 is dissolved. To the second solution 311 is added an active targeting ligand 313 that conjugates to the sorafenib 312. In one embodiment, the first solution 301 and second solution 311 are precipitated separately to form doxorubicin nanoparticles 303 and sorafenib nanoparticles 314, respectively, in solution. The nanoparticles 303 and 314 are then aggregated to form the particle formulation 300.

In another embodiment illustrated in FIG. 3B, the particle formulation 350 is obtained as nanoparticles 350 in which the therapeutic agents doxorubicin 302 and the sorafenib 312 are present as a mixture. The first solution 301 and second solution 311 are prepared as previously described in relation to FIG. 3A. To the second solution 311 is added an active targeting ligand 313 that conjugates to the sorafenib 312. In the next step, the solutions 301 and 311 are mixed together to obtain a solution 320 containing both therapeutic agents 302 and 312 dissolved in proteins or polysaccharides, with the sorafenib 312 conjugated to active targeting ligand 313. Finally, the nanoparticle formulation 350 is formed by precipitating from the composite solution 320. The precipitation could be done by alcohol coacervation in one embodiment.

In one embodiment illustrated in FIG. 3C, a core-shell nanoparticle formulation 400 for treating a patient with hepatocellular carcinoma is disclosed. In one embodiment, the formulation comprises one or more proteins or polysaccharides to form a core 401 and one or more proteins forming a shell 402, the core 401 and the shell 402 each comprising one or more therapeutic agents. In one embodiment the core 401 is formed of polyvinyl alcohol (PVA) 410 loaded with doxorubicin 411 and the shell 402 is formed of albumin 420 and loaded with sorafenib 421 as a therapeutic agent to form the core-shell nanoparticle 400. In one embodiment, the shell 402 is conjugated with an active targeting agent 403 such as transferrin to deliver the therapeutic agents to the targeted tissue.

Figure 4:
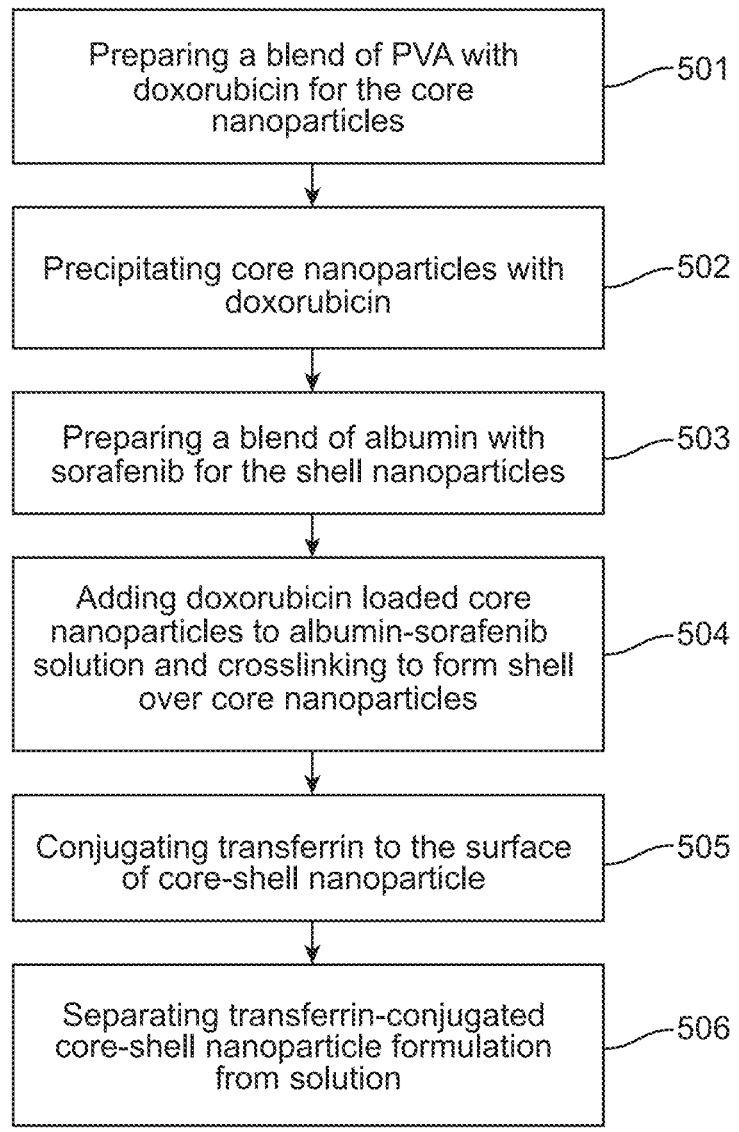
FIG. 4 is a schematic of the method of preparing a core-shell formulation for treating a patient with hepatocellular carcinoma according to one embodiment.

In one embodiment of the method illustrated in FIG. 4, the particle formulation 400 is obtained using the steps shown in the figure with reference to the embodiments illustrated in FIG. 3C. In step 501, the polyvinyl alcohol (PVA) 410 solution to form the core 401 is reacted with the hydrophilic drug such as doxorubicin 411. In the next step 502, the polyvinyl alcohol (PVA) 410 is precipitated to form the doxorubicin-loaded core nanoparticles 412. In the following step 503, sorafenib 421 is blended with albumin 420 solution for forming the shell 402 of the formulation. The albumin 420 and the sorafenib 421 form an aggregate 422 in solution. The doxorubicin-loaded core nanoparticles 412 are then coacervated with the aggregates 422 in step 504, in which the sorafenib 421 is incorporated into the albumin 420 and crosslinked to form a shell 402 around the core 401 using an alcohol coacervation process.

In step 505, the fully formed core-shell nanoparticles 430 with the doxorubicin 411 loaded in the core 401 and the sorafenib 421 loaded in the shell 402 are conjugated to an active targeting agent 403. In one embodiment the targeting agent 403 is transferrin. Finally, in step 506, the transferrin-conjugated core-shell nanoparticle formulation 400 is separated from solution for therapeutic use.

In one embodiment, the nanoparticle formulation disclosed could be configured to release therapeutic agents that are hydrophilic or hydrophobic. In various embodiments shown in FIG. 3A-3C, the protein or polysaccharides is selected from polyethylene glycol, polyethylene oxide, starch, hyaluronic acid, gelatin, Poly(vinyl alcohol-co-ethylene), poly(vinyl butyral-co-vinyl alcohol-co-vinyl acetate), poly(vinyl chloride-co-vinyl acetate-co-vinyl alcohol), poly-N-para-vinylbenzyl-lactonamide, chondrotin sulphate, dextran, cyclodextrin, polyglycolide (PGA), glycolide L-lactide copolymers (PGA/PLLA), glycolide/trimethylene carbonate copolymers (PGA/TMC), polylactides (PLA), poly-L-lactide (PLLA), Poly-DL-lactide (PDLLA), L-lactide/DL-lactide copolymers, lactide/tetramethyl-glycolide copolymers, poly-caprolactone, poly-valerolacton, poly-hydroxy butyrate, poly vinyl alcohol (PVA) polyhydroxy valerate, poly-N-isopropylacrylamide (p-NIPPAAM) and lactide/trimethylene carbonate copolymers, polyvinyl pyrrolidone (PVP), polyethylene imine (PEI), chitosan, carboxymethyl chitosan, chitin, pullulan, dextrose cellulose, carboxymethyl cellulose, alginate, glucomannan, poly-γ-glutamic acid, poly propylene glycol, poly acrylic acid, poly(lactic-co-glycolic acid) (PLGA), poly-caprolactone (PCL), poly-hydroxy butyrate (PHB), polyvinylpyrrolidone (PVP), Polyethyleneimine (PEI) and lactide/trimethylene carbonate copolymers, and their derivatives, or combinations thereof.

In various embodiments shown in FIG. 3A-3C, the protein is chosen from human serum albumin, bovine serum albumin, protamine, transferrin, lactoferrin, fibrinogen, gelatin, mucin, soy protein, apoferritin, ferritin, lectin, gluten, whey protein, prolamines such as gliadin, hordein, secalin, zein, avenin, ovalbumin, histone, fibrin, collagen, and their derivatives or combinations thereof. In one embodiment, the total size of the core-shell particle is of 1-1000 nm. In one embodiment, the optimized dosage of doxorubicin 411 in poly vinyl alcohol (PVA) core 401 of the formulation is 2 µM and that of sorafenib 421 in albumin shell 402 is 5 µM against hepatocarcinoma cells.

In various embodiments the nanoparticles or the core or the shell thereof is formed by a method selected from solvent evaporation or nanoprecipitation or micro emulsion or double emulsion or spontaneous emulsification or solvent diffusion or salting out or emulsification-diffusion or supercritical fluid technology or electrospray or electro deposition or ultrasonication or spray drying or physical or chemical cross linking techniques, desolvation, heat denaturation, alcohol coacervation, super saturation, emulsification, electrospray, or combinations thereof.

In various embodiments the therapeutic agents are entrapped within the core or the shell of the particle by a using physical cross-linking methods like freeze-thawing, self-assembly or ultrasonication, microwave assisted aggregation, gamma irradiation, UV irradiation, or simple desolvation, coacervation, complex coacervation, nano-precipitation, sol-gel, spray drying, salting-out, cross linking using hydrophobic nanoparticles and/or chemical cross linking methods like oxidation-reduction, free radical induced ring opening polymerization, polymerization of the monomer using suitable cross-linkers freeze-thaw technique, or other technique known in the art.

In various embodiments, a method of treatment against cancer, inflammatory or auto-immune diseases is disclosed, comprising delivering to targeted tissue, a therapeutically effective amount of a formulation comprising the core-shell nanoparticles as illustrated in various earlier embodiments. The method in various embodiments may involve administering the formulation to a human patient by local injection, intratumoral, intraarterial, using catheters (transarterial chemoembolization route for implantation), intrathecal, intracavitary, intravenous, subcutaneous, intramuscular or oral delivery. The method in some embodiments may target the therapeutic agents to specific tissue.

In one embodiment, a method of treating a patient for hepatocellular carcinoma is disclosed, comprising administering to a patient, a therapeutically effective amount of a formulation comprising the core-shell nanoparticles as illustrated in FIG. 3A-C. In one embodiment, the protein of the shell is conjugated with a ligand for targeting hepatocellular carcinoma tissue. In one embodiment, the formulation preferentially aggregates to the hepatocellular carcinoma tissue, and releases the therapeutic agents from the core and the shell. In one embodiment, the polymer core is a polyvinyl alcohol (PVA), the protein shell is an albumin shell and the ligand for targeting tissue is transferrin as an active targeting agent.

The method in some embodiments may involve either simultaneous release of the therapeutic agents from the core of the nanoparticles, and in other embodiments the agents may be released sequentially, as required. In some embodiments, the method may use passive targeting of tissue, while in other embodiments the therapeutic agents are delivered by active targeting. In some embodiments of the method the nanoparticles are tracked in vivo using one or more of optical, magnetic or x-ray contrast.

The particle formulations disclosed in the various embodiments above are configured to independently release first therapeutic agents 102 from the core 101 and second therapeutic agents 104 from the shell 106. This gives the nanocarrier an extraordinary ability to deliver multiple therapeutic molecules directly to specific cells rather than systemically to all cells and, further, to deliver both the drugs into the cell, thereby potentially reducing dosages at equivalent efficacy. Further the use of two separate protein phases is envisioned, rather than synthetic materials as in engineered nanoparticles. Use of proteins as a nanocarrier is considered because of the reduced toxicity of such natural materials. A second part of this invention is the modification of one or more of the proteins by doping/embedding them with metallic nanoclusters of gold or other suitable metals nanoclusters for imparting specific characteristic properties to the nanocarrier such as optical/magnetic/x-ray contrast. This enables tracking of the nanoparticles in-vivo and understanding their bio-distribution and location.

One application wherein such a drug delivery system can be especially useful is in cancer or tumor formation. Tumorigenesis is a multi-step process, where the genetic alterations enable the cancer cells to acquire properties such as self-sufficiency of growth signals, insensitivity to anti-growth signals evasion of apoptosis, limitless replicative potential, sustained angiogenesis which further lead to tissue invasion and metastasis. Unlike the cytotoxic chemotherapeutic drugs, protein kinase inhibitors target specifically the protein kinases, which are deregulated (constitutively activated/mutated/over-expressed) in cancer cells. Moreover, most of the kinase inhibitors have been found to have low levels of undesirable side effects in clinical and preclinical studies compared to cytotoxic drugs. Yet, for highly aggressive and metastatic cancers, cytotoxic drugs present an immediate effect compared to kinase inhibitors. Resistance to kinase inhibitors in the long run due to point mutations in the drug-binding domain of kinases eventually distorts the conformation of drug binding domain and hence prevents the drug from binding to it. In certain cases, kinase inhibition of the primary oncoprotein can lead to the activation or over-expression of a secondary survival signal in the oncogenic network. In those cases monotherapy with a single therapeutic agent remains ineffective. Combination of cytotoxic chemotherapeutic drugs and kinase inhibitors can be an attractive approach to treat highly aggressive tumor masses. The current invention enables combination therapy using bio-friendly protein based nanocarriers, and attempts to solve most of the issues associated with conventional treatment strategy.

The invention is further illustrated with reference to the following examples, which however, are not to be construed to limit the scope of the invention as defined by the appended claims.

EXAMPLES

Example-1

Synthesis of (Protamine-Rapamycin) Nanocore

Synthesis of protamine-rapamycin nanocore: protamine-rapamycin nanocore was prepared using aqueous chemical route. The cationic peptide protamine (10 kDa) was dissolved at a concentration of 11 mg/ml in nuclease and endotoxin free water. Rapamycin was dissolved in DMSO as per the manufacturer's instructions. Rapamycin was added to aqueous solution of protamine. The complexation of protamine and rapamycin resulted in a turbid solution, which was vortexed vigorously and incubated at room temperature for 30 min to enable the effective complexation of rapamycin with protamine. Thus formed protamine-rapamycin nanocore was purified by dialysis using 2 kDa cut off dialysis membrane.

Synthesis of (Protamine-Rapamycin)-(Albumin-Dasatinib) Core-Shell Nanomedicine:

Dasatinib in DMSO was mixed with aqueous solution of albumin at a dasatinib final concentration of 100 µM. In a typical synthesis, 100 µM dasatinib in albumin was added drop-wise to protamine-rapamycin solution. The solution was kept under continuous stirring for ~30 m at room temperature. The individual HSA molecules were cross-linked using 2 mg 1-Hhyl-3-[3dimethylaminopropyl]carbodiimide hydrochloride (EDC), a zero-length cross-linker for effective entrapment of the therapeutic molecules m the protein shell. The reaction was continued for ~2 h at room temperature. The solution was further subjected to dialysis using dialysis cassettes with 2 kDa molecular weight cut off and lyophilized for 48 h. The percentage entrapment of the drug was determined from standard graph of rapamycin and dasatinib.

Example-2

Computational Modeling of (Protamine-Rapamycin)-(Albumin-Dasatinib) Core-Shell Nanomedicine The computational modeling of two different drug molecules (rapamycin and dasatinib) docked to two different proteins (protamine and albumin) in a core-shell architecture is designed. Computational modeling of albumin-dasatinib and protamine-rapamycin interactions is shown in FIG. 5A and computationally designed structure of (protamine-rapamycin) (albumin-dasatinib) core-shell nanoparticles is shown in FIG. 5B.

Figure 6B:
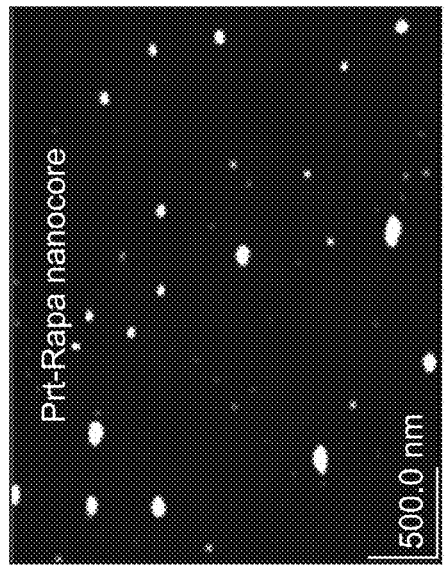
FIGS. 6A-C illustrate the size distribution of (protamine-rapamycin) and (albumin-dasatinib) core-shell system.
Figure 6C:
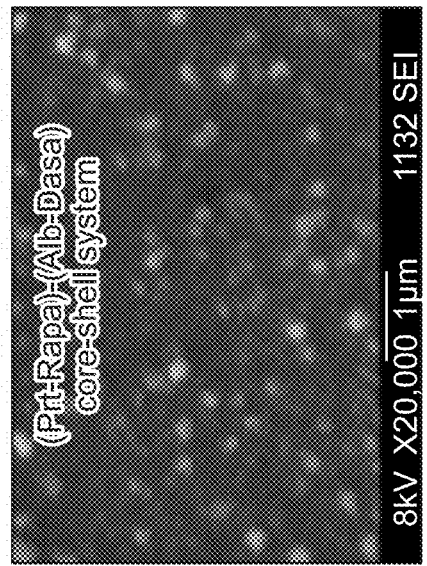
Figure 6A:
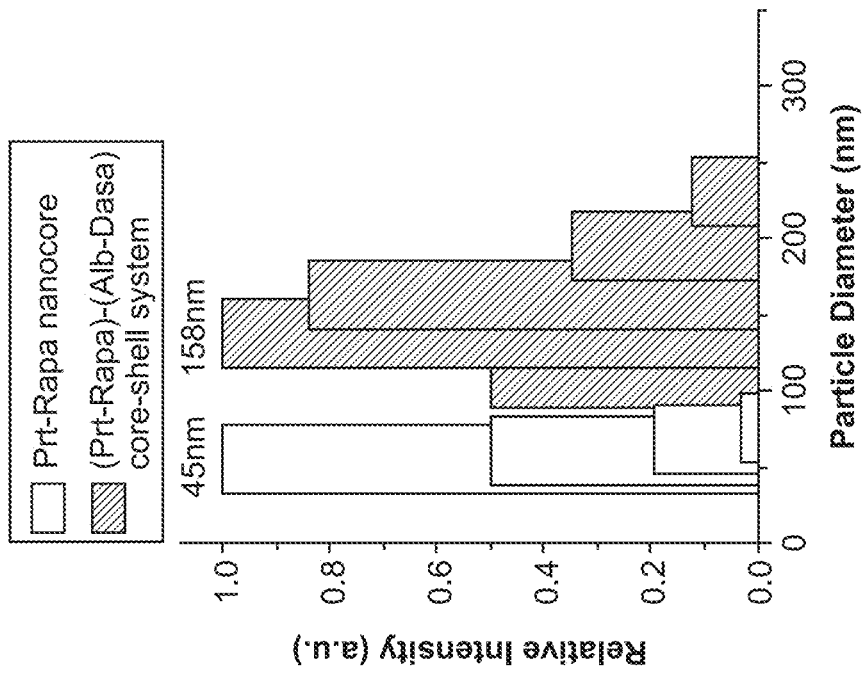
Figures 7A, 7B:
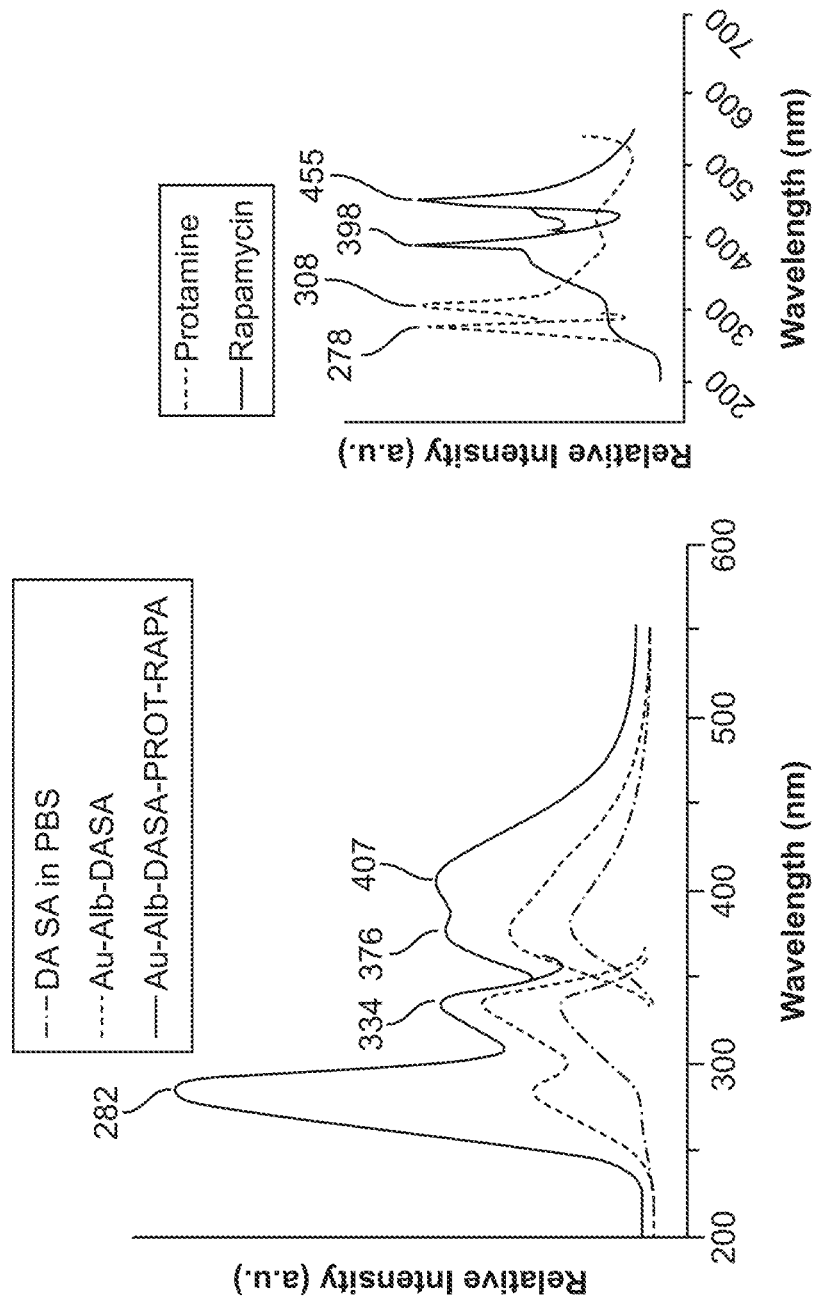
FIG. 7A and FIG. 7B show the photoluminescence spectra of (protamine-rapamycin) and (albumin-dasatinib) core-shell system, where albumin is doped with metallic nanoclusters of gold.
Figure 8A:
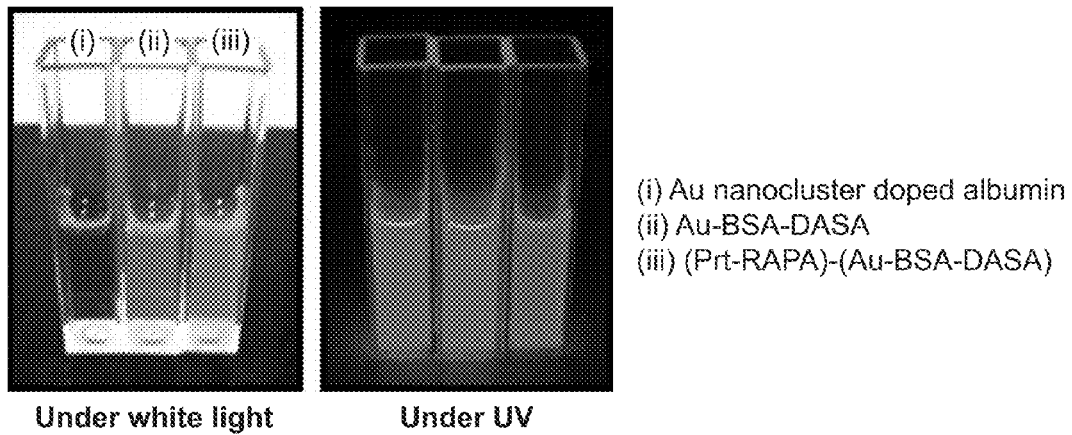
FIG. 8A show the red-NIR emission from gold nanocluster doped protein-protein core-shell nanomedicine and FIG. 8B show the corresponding photoluminescence excitation-emission spectrum.
Figure 8B:
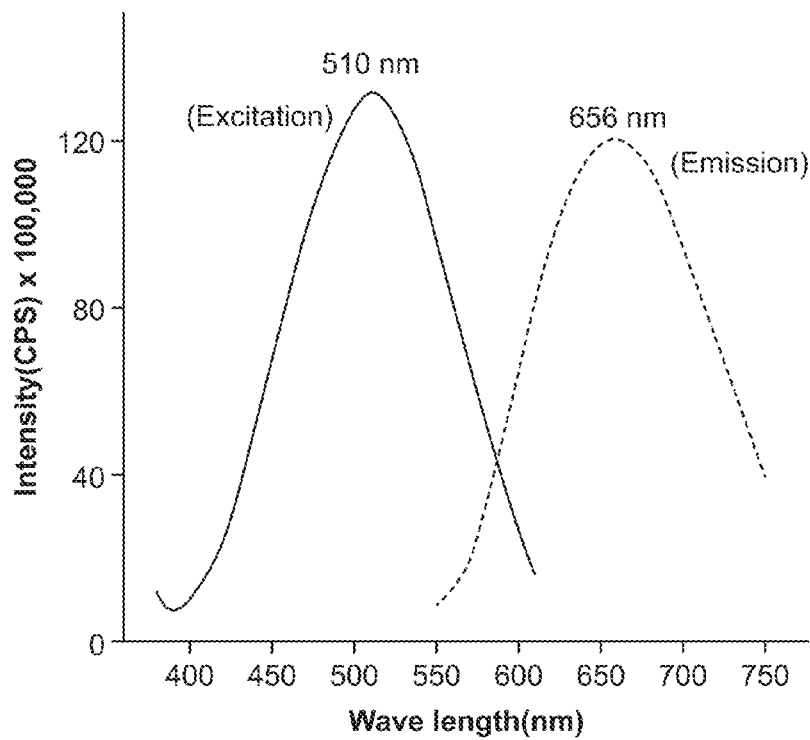

Characteristics of (Protamine-Rapamycin)-(Albumin-Dasatinib) Core-Shell Nanomedicine:

FIG. 6 shows an example of the result with the size distribution of (protamine-rapamycin) and (albumin-dasatinib) (FIG. 6A) core-shell system using dynamic light scattering (DLS) showing a core of size around 45 nm and a core-shell structure of size around 158 nm (FIG. 6B) atomic force microscopy (AFM) and (FIG. 6C) scanning electron microscopy showing the spherical morphology of the particles formed. The photoluminescence spectra of (protamine-rapamycin) and (albumin-dasatinib) core-shell system, where albumin is doped with metallic nanoclusters of gold is shown in FIGS. 7A and 7B. Further, the red-NIR emission from gold nanocluster doped protein-protein core-shell nanomedicine and the corresponding photoluminescence excitation-emission spectrum is shown in FIGS. 8A and 8B.

Example-3

Results of Nanomedicine Treatment Against Breast Cancer

Figure 9:
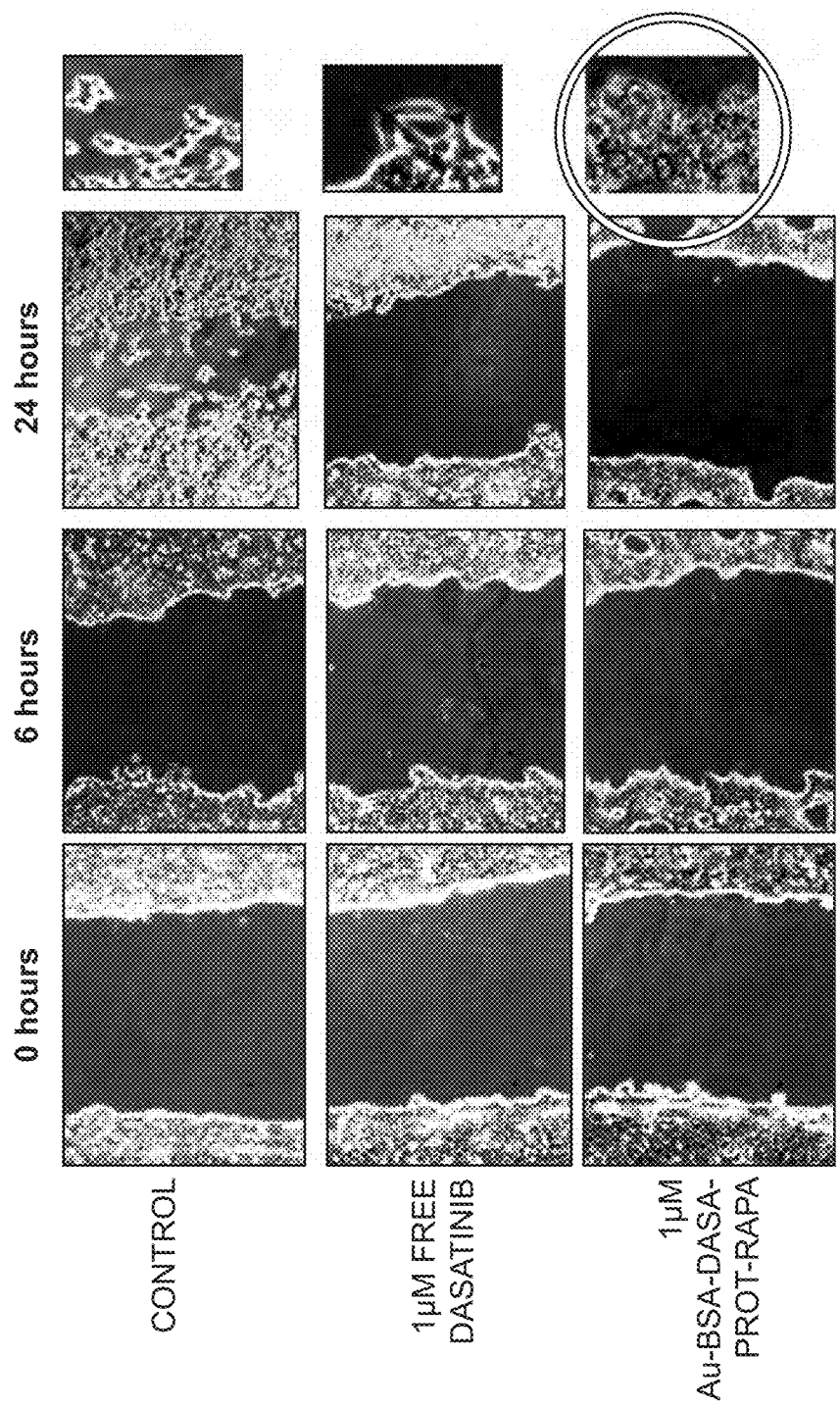
FIG. 9 is illustrates the improved efficacy of the (prt-rapa)-(alb-dasa) core-shell nanomedicine in cancer cell migratory potential. The encircled image shows the distorted morphology of breast adenocarcinoma cells treated with the protein-protein core-shell nanomedicine comprising of gold nanocluster doped (prt-rapa)-(alb-dasa).

The protamine-rapamycin) and (albumin-dasatinib) core-shell nanomedicine is administered either intravenously, orally, parenterally, subcutaneously or by direct local delivery. The method of treatment of cancer-like diseases using core-shell nanomedicine aiding combinatorial anti-cancer therapy by sequential or simultaneous delivery of a combination of small molecule kinase inhibitor and chemodrugs. of the (prt-rapa)-(alb-dasa) core-shell nanomedicine in cancer cell migratory potential shows an improved efficacy in FIG. 9. The encircled image shows the distorted morphology of breast adenocarcinoma cells treated with the protein-protein core-shell nanomedicine comprising of gold nanocluster doped (prt-rapa)-(alb-dasa). FIG. 10 shows the destabilization of cytoskeleton and distortion of cellular morphology by (protamine-rapamycin) and (albumin-dasatinib) core-shell system as depicted by actin staining.

Example-4

Synthesis of Core-Shell Nanomedicine Against Hepatocellular Carcinoma (Liver Cancer)

Hepatocellular carcinoma is an aggressive disease that is typically diagnosed late and has median survival of ~6 months for majority of patients and ~20 months for <5% of patients having localized lesions. Although surgical resection is the mainstay therapy, most of the patients are not eligible for surgery because of the extent of tumor spread and underlying liver dysfunction. In these patients, systemic chemotherapy is the standard of care. A multikinase inhibitor, sorafenib, and doxorubicin (Dox) in the form of implantable microbeads (DC Beads®), are the two FDA-approved formulations used in the clinics. However, as single agents, these drugs give only limited therapeutic outcome. So, a multifunctional nanoparticle is developed to play an integrated role for effectively combating various cancers. Therefore, on inhibiting the critical kinase signaling by sorafenib together with DNA intercalation by Dox may yield synergistic anti-tumor effect in liver cancer. Accordingly, lead to the development of a hepatocellular carcinoma (HCC)-targeted core-shell nanoparticle, capable of delivering both sorafenib and doxorubicin together. In order to optimally design the nano-construct, prior to wet chemical realization, in silico docking simulation was employed.

Example-5

In Silico Molecular Docking

Figure 11A:
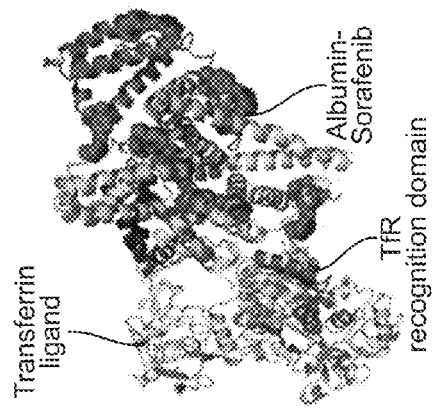
FIG. 11A shows the in silico docking simulation of the albumin loaded with sorafenib.
Figure 11B:
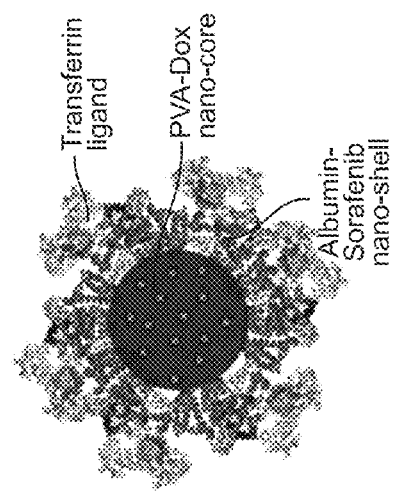
FIG. 11B shows the in silico docking model of transferrin-docked albumin-sorafenib nano-shell with TfR recognition domain.
Figure 11C:
FIG. 11C shows the in silico model of transferrin-docked albumin-sorafenib nano-shell with transferrin receptor.
Figure 11D:
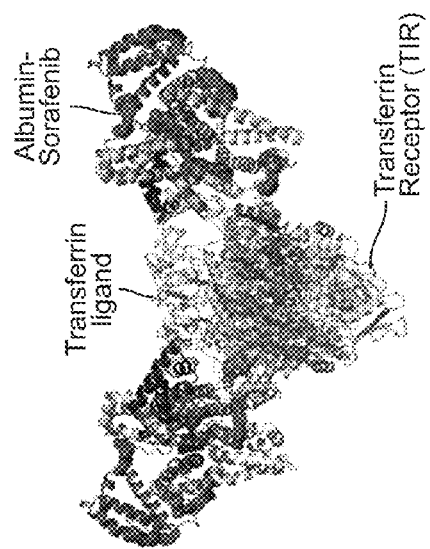
FIG. 11D shows the simulated model of TfR-targeted albumin-sorafenib nano-shell formed over PVA-Dox nano-core.

In silico investigation of loading sorafenib in albumin indicated that at least 6 molecules of sorafenib can be loaded into single molecule of albumin without significant cross-talk (FIG. 11A). Prior to nanoparticle preparation, TfR recognizing amino acid residues of transferrin ligand are affected during its interaction with sorafenib-loaded albumin nano-shell are investigated. Docking results indicated that carboxylic (FIG. 11B) as well as amino terminal lobe of transferrin which is typically recognized by TfR, remains intact when the targeting ligand interacts with albumin-sorafenib nano-shell. Furthermore, transferrin was found to interact with certain specific amino acid residues of albumin that are different from sorafenib binding sites (FIG. 11B), indicating that the interaction of transferrin with the nano-shell does not interfere with the existing hydrophobic interactions between albumin and sorafenib. FIG. 11C shows the in silico model of transferrin-docked albumin-sorafenib nano-shell being recognized by TfR, and FIG. 11D shows simulated model of TfR-targeted albumin-sorafenib nano-shell formed over PVA-Dox nano-core. Thus, the in silico approaches have provided certain indicative information on the interaction of a drug/targeting ligand with a nano-carrier/receptor.

Example-6

Preparation and Physicochemical Characterization

Following the in silico design, the core-shell nanoparticles were prepared by a two-step wet chemical process. Schematic representation of the synthesis is shown in FIG. 12A. At first, Dox loaded polymer nano-core was prepared using freeze-thaw process and a nano-shell of albumin-sorafenib was formed over the nano-core by employing ethanol coacervation. FIG. 12B shows atomic force microscopy (AFM) image of PVA-Dox nano-core indicating size ~90 nm. FIG. 12B inset presents hydrodynamic diameter of the core as determined by dynamic light scattering (DLS), which is in consistence with the AFM measurement. FIG. 12C displays scanning electron microscopy (SEM) image of core-shell particles showing an overall size ~110 nm, and the corresponding DLS graph also confirmed the same. TEM image (FIG. 12C inset) clearly indicated the formation of a unique shell over the polymer nano-core, suggesting the thickness of the shell is ~20 nm. Drug loading and encapsulation efficiency of Dox in PVA nano-core were 3% and 82%, respectively, and that of sorafenib in albumin nanoshell were 2.4% and 91%, respectively.

FT-IR Studies:

After characterizing the morphology, Fourier transform infrared spectra (FT-IR) of PVA-Dox nano-core (PD), TfR-targeted albumin-sorafenib nano-shell (AST), and core-shell nanoparticles were individually shown in FIG. 12D. Presence of infrared peaks at 3531 $cm^{-1}$ and 3328 $cm^{-1}$ indicated O—H stretching vibration in PVA and Dox. The same peaks also overlapped with stretching vibrations in N—H bonds in primary amine groups of Dox. Stretching vibration in C═O groups, bending vibration in N—H bonds, and C—C stretching vibration arising from aromatic rings of Dox were indicated by IR peaks at 1732 $cm^{-1}$, 1583 $cm^{-1}$, and 1415 $cm^{-1}$ respectively. The presence of C═O stretching vibration resulting from secondary alcohol groups of PVA was indicated by peak at 1235 $cm^{-1}$. In the nano-shell, possibility of forming hydrogen bonds between nitrogen atoms of sorafenib and amino acid residues in albumin was indicated by N—H stretching vibration peak at 3327 $cm^{-1}$. FT-IR peaks at 1655 $cm^{-1}$, 1537 $cm^{-1}$, and 1396 $cm^{-1}$ indicated amide-I, II, and III groups respectively in albumin and transferrin. The core-shell nanoparticles displayed additive IR peaks of nano-core and nanoshell.

Example-7

Drug Release Studies

Following FT-IR studies, drug release profile from the core-shell particles was studied using a spectrophotometer. FIG. 12E indicates that both sorafenib and Dox are released in a sustained manner in cell-free aqueous medium (PBS) with ~10% release in the first 24 h. Thereafter, ~50% release was observed for sorafenib in the aqueous medium for 3 weeks. In contrast, although Dox hydrochloride is relatively hydrophilic, controlled release was observed from the PVA core, with ~30% of Dox getting released for 21 days.

Transferrin Receptor Expression and Cellular Uptake:

In the next step, the expression of TfR in HepG2 cells was studied using flow cytometry. FIG. 13A shows unstained cells (control). ~76% of the malignant cells were found to express TfR before iron chelation as noticed from FIG. 13B. After creating an iron deficient microenvironment by treating the cells with 100 μM DFO, the number of the TfR-expressing cells increased to ~89% (FIG. 13C). FIG. 13D shows that upon addition of iron-loaded transferrin (holotransferrin), the number was reduced to ~42%. Following that, intracellular uptake of the core-shell nanoparticles in cancer cells was investigated. FIG. 13E shows that untargeted particles are taken-up by only ~70% of HepG2 cells. Upon conjugating the nanoparticles with transferrin, the uptake was effectively increased to ~83% as shown in FIG. 13F. After creating iron-deficient microenvironment, the uptake was further increased to ~94% (FIG. 13G) due to the increase in the number of TfR expressing cells. Upon addition of iron-loaded transferrin, the uptake was dropped to ~69% due to the saturation of TfR expression in these cells (FIG. 13H).

Example-8

Cytotoxicity Studies

Figure 14A:
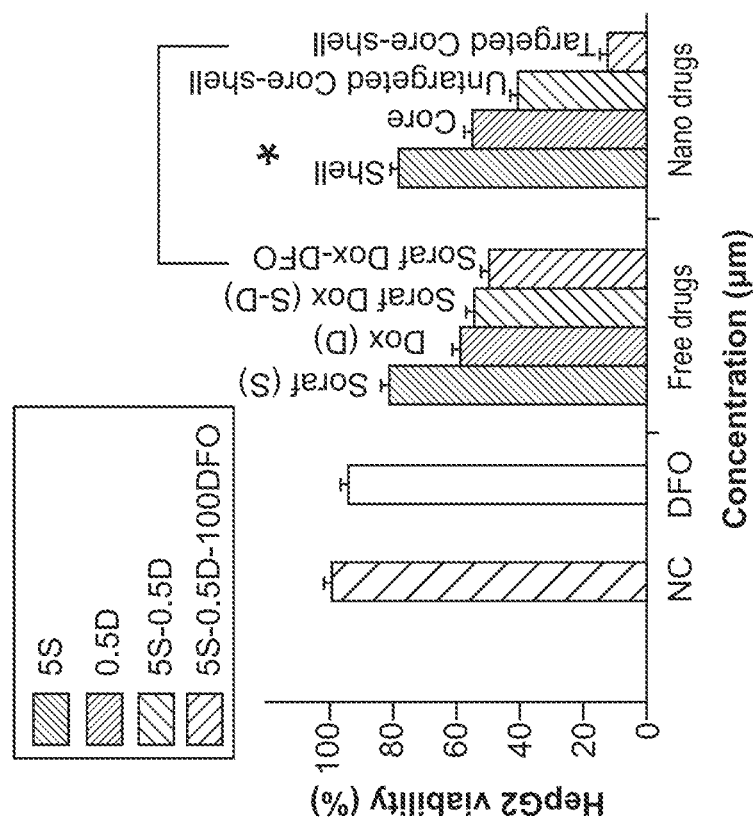
FIG. 14A shows the viability of HepG2 cells after core-shell nanomedicine treatment by alamar blue assay method and FIG. 14B shows confocal image of apoptotic cells and damaged nucleus after nanomedicine treatment.

After confirming the uptake, cytotoxicity of the core-shell nanoparticles was studied in HepG2 and PLC/PRF/5 cells using alamar blue assay. The study was performed before and after enhancing TfR expression in the cells. As noticed from FIG. 14A, the free drug combination (5 μM sorafenib (5S) and 0.5 μM Dox (0.5D)) could produce only ~50% cytotoxicity. Even after creating iron depleted microenvironment by pretreating HepG2 with 100 μM DFO, the cell death imparted by free drug combination did not improve further. Compared to this, untargeted nanoparticles (containing 0.5 μM Dox in nano-core and 5 μM sorafenib in nano-shell) showed improved toxicity, however, only up to ~63%.

In contrast, TfR-targeted core-shell nanoparticles registered ~92% synergistic cell death in the TfR overexpressing HCC cells. Similar trend in cytotoxicity was also observed in mutant p-53 HCC cell, PLC/PRF/5. Further, the drug-free core-shell nanoparticles did not exert any toxicity towards the cancer cells, suggesting that the observed cytotoxicity is exclusively due to the combined effect of chemodrugs in the nanoparticles.

Figure 14B:
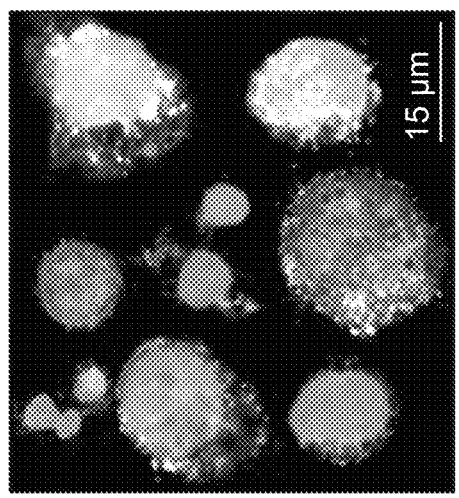

Apoptosis Studies:

In the next step, the mode of cell death using Annexin V/PI apoptosis assay was investigated. FIG. 14B shows core-shell nanoparticles (containing 5 μM sorafenib in albumin shell and 0.5 μM Dox in PVA core) treated cells displaying classical features of apoptosis such as extensive plasma membrane blebbing and separation of cell fragments into green fluorescent apoptotic bodies during the budding process. Red staining in the nucleus indicates that the DNA is also damaged during apoptosis. The apoptotic cells using flow cytometry were also quantified. FIG. 15A shows untreated cells (negative control, NC). FIG. 15B and FIG. 15C shows that both sorafenib and Dox as individual free drugs could exert only ~38% and ~53% apoptosis, respectively. Even after combining both the drugs (5 μM sorafenib (5S) with 0.5 μM Dox (0.5D)), a maximum of only ~60% apoptosis was registered (FIG. 15D). In contrast, as separate nanoformulations, the nano-shell (containing 5 μM sorafenib, (5AST) (FIG. 15F), and the nano-core (containing 0.5 μM Dox, (0.5PD) (FIG. 15G) have shown slight improvement in apoptosis (~39% by shell, and ~61% by core). After combining the two in a core-shell targeted fashion, excellent apoptosis was registered in ~91% cells (FIG. 15H). Interestingly, pretreating the cells using 100 pMDFO (100DFO) did not affect the viability of TfR overexpressing cells (FIG. 15E).

Example-9

Development and Characterization of 3D HCC Spheroids

For studying the cytotoxicity of the nanoparticles in 3D microenvironment culture, HCC spheroids were developed. ~3.75×104 cells dispersed in 5 μL volume were used to prepare each individual spheroid. FIG. 16A displays the morphology of alginate-collagen based cell-free spheroids, and FIG. 16B shows 3D spheroids embedded with HCC cells after 5 days of culture, where the cancer cells were found to attach and effectively proliferate in the 3D microenvironment. FIG. 16C presents the magnified image depicting uniform spreading of liver cancer cells throughout the spheroid (size ~200 μM). After 15 days of culture, enhanced proliferation of cells leading to HCC tissue like architecture was clearly evident in the 3D system (FIG. 17A). At this stage, each spheroid contained ~1.8×105 cells, as indicated by the metabolic activity measurement using alamar blue assay. FIG. 17B shows the consistent increase in resorufin absorbance from the proliferating cells in the 3D environment in a time dependent manner. FIG. 18A-E shows depth-by-depth confocal view of the spheroid, where aggregation of individual tumor cells forming HCC tissue-like phenotype can be clearly seen from anterior (top) to posterior side (bottom) of the spheroid.

Figures 19A, 19B, 19C, 19D:
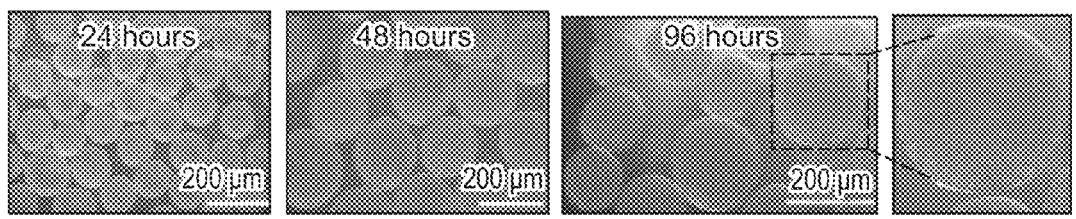
FIG. 19A shows the uptake of core-shell nanomedicine by HCC spheroids after 24 h of incubation.
FIG. 19B shows the uptake of core-shell nanomedicine by HCC spheroids after 48 h of incubation.
FIG. 19C shows the uptake of core-shell nanomedicine by HCC spheroids after 96 h of incubation.
FIG. 19D Magnified stereo microscopy image shows the uptake of core-shell nanomedicine by almost all the cells in the spheroid.

Nanoparticle Uptake in 3D Spheroids:

After the successful preparation, the uptake of core-shell nanoparticles by cells in the 3D spheroid using stereo microscopy was investigated. FIG. 19A-C shows the uptake after 24 h, 48 h, and 96 h of incubation, respectively. Clearly, with increase in the incubation period, the color of the spheroid turned from dull to deep orange (color emerged from Dox in the nano-core), indicating that the cancer cells in the 3D culture effectively uptake the core-shell particles in a time-dependent manner.

Figures 20A, 20B, 20C:
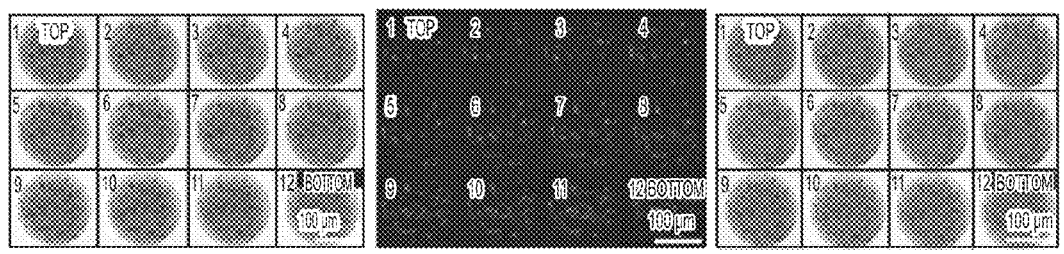
FIG. 20A shows the section-by-section confocal imaging displays bright field view of the uptake.
FIG. 20B shows the fluorescence emitted from doxorubicin in nano-core and FIG. 20C shows the merged view (bright field and fluorescent) of the uptake by the spheroid (96 h).

It may be noticed that the size of the spheroids also gradually increased from ~70 μM to ~200 μM upon prolonged incubation. This is due to the swelling property attributed to hydrophilic nature of the alginate based 3D culture system. Depth-by-depth imaging of the spheroid by confocal microscopy further confirmed the uptake (96 h) in the 3D environment (FIG. 20A-C). FIG. 20A displays bright field image of nanoparticles being taken-up by cancer cells. The uptake was confirmed by the fluorescence emission of Dox from nanoparticle internalized cells in the spheroid (FIG. 20B). FIG. 20C presents the merged view of bright field and fluorescent images from anterior (top) to posterior (bottom) side of the spheroid. This confirms the effective uptake of the core-shell particles by almost all the cells in the 3D culture environment.

Example-10

Cytotoxicity Studies in 3D Spheroids

Figure 21A:
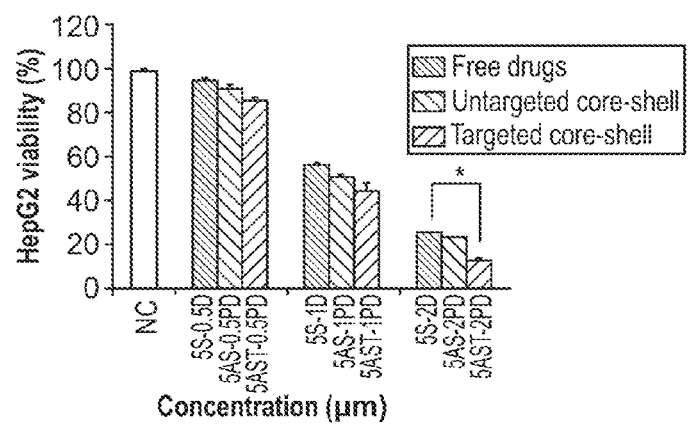
FIG. 21A shows the cytotoxicity in the spheroid after core-shell nanomedicine treatment (96 h) by alamar blue assay method.

After confirming the cellular uptake, cytotoxicity of the core-shell nanoparticles in the spheroids was studied using alamar blue assay. Interestingly, the cytotoxicity in the 3D environment varied considerably compared to that of the 2D culture (FIG. 21A). Targeted core-shell particles (containing 5 μM sorafenib in albumin shell (5AST) and 0.5 μM Dox in PVA core (0.5PD)), which has imparted ~92% cell death in the 2D culture, showed only ~10% cytotoxicity in the 3D spheroid. Even after modulating Dox concentration, the free drug combination (5 μM sorafenib (5S) and 2 μM Dox, (2D)), and equimolar concentration of untargeted nanoparticles (5 μM sorafenib in albumin nano-shell (5AS) and 2 μM Dox in PVA nano-core (2PD)) has registered only ~70% cytotoxicity in the 3D cell culture system. In contrast, HCC spheroids treated with TfR-targeted core-shell nanoparticles (5 AST-2PD) exhibited ~93% synergistic toxicity in the iron-deficient 3D microenvironment.

Figures 21B, 21C, 21D:
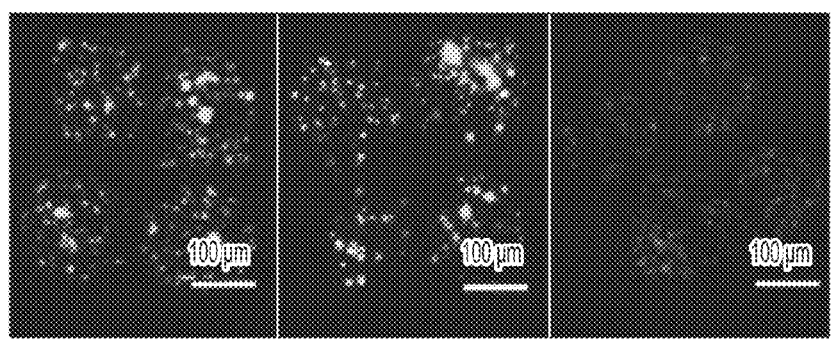
FIG. 21B shows the cell viability in the untreated HCC spheroid determined by live-dead assay method.
FIG. 21C shows the cell viability in the treated HCC spheroid with low concentration of core-shell nanoparticles determined by live-dead assay method.
FIG. 21D shows the cell viability in the treated HCC spheroid with optimized concentration of core-shell nanoparticles determined by live-dead assay method.

Live-Dead Staining in 3D Spheroids:

Cytotoxicity assay performed in the HCC spheroids was visually validated using live-dead assay, before and after nanoparticle treatment (FIG. 21B-D). FIG. 21B shows that untreated, metabolically active cancer cells selectively internalized calcein dye thereby showing bright green fluorescence in the 3D environment. Upon treatment with core-shell nanoparticles containing low concentration of Dox (5 μM sorafenib in TfR-targeted albumin shell (5AST) and only 0.5 μM Dox in PVA core (0.5PD)), much of the cells in the spheroid still managed to survive better, and only few underwent cell death as shown in the FIG. 21C. However, upon optimizing the concentration of Dox in the nanocore to 2 μM, almost all the malignant cells in the spheroid were found to be dead in the TfR expression enhanced 3D microenvironment (FIG. 21D). Thus, by simultaneously inhibiting aberrantly active oncogenic kinase and imparting cytotoxic stress using a TfR-targeted nanomedicine containing two FDA approved drugs, doxorubicin and sorafenib, promising synergistic toxicity can be achieved against hepatocellular carcinoma cells.

What is claimed is:

1. A method of treating a patient for hepatocellular carcinoma with a formulation comprising therapeutic agents comprising:
  a. forming a first solution of doxorubicin comprising one or more proteins or polymers;
  b. conjugating sorafenib with an active targeting ligand with one or more proteins to form a second solution;
  c. producing a formulation comprising nanoparticles using the first and the second solutions; and
  d. administering the nanoparticle formulation to a patient such that the targeting ligand causes the formulation to preferentially segregate to the hepatocellular carcinoma tissue to release the therapeutic agents;
  wherein the nanoparticles comprise polyvinyl alcohol forming a core and human serum albumin forming a shell;
  wherein the doxorubicin and the sorafenib are loaded onto the same nanoparticle such that doxorubicin is loaded onto the core and sorafenib is loaded onto the shell;
  wherein the ligand for targeting comprises transferrin; and
  wherein the formulation is administered by intraarterial delivery.

2. The method of claim 1, wherein the producing the nanoparticle formulation comprises one of:
  precipitating nanoparticles comprising the doxorubicin and the sorafenib separately from the first and the second solutions and aggregating the nanoparticles into the nanoparticle formulation,
  mixing the first and the second solutions and precipitating composite nanoparticles to produce the nanoparticle formulation, or
  forming a core nanoparticle comprising doxorubicin using the first solution and a shell comprising sorafenib over the core nanoparticle using the second solution to form the nanoparticle formulation.

3. The method of claim 1, wherein the formulation results in cytotoxicity greater than 90% against hepatocellular carcinoma tissue at minimum concentrations of doxorubicin in core of 2 μM and sorafenib in shell of 5 μM.

\* \* \* \* \*